United States Patent
Itu et al.

(10) Patent No.: US 10,622,102 B2
(45) Date of Patent: Apr. 14, 2020

(54) PERSONALIZED ASSESSMENT OF BONE HEALTH

(71) Applicant: Siemens Healthcare GmbH, Erlangen (DE)

(72) Inventors: Lucian Mihai Itu, Brasov (RO); Costin Florian Ciusdel, Azuga (RO); Puneet Sharma, Monmouth Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 368 days.

(21) Appl. No.: 15/441,347

(22) Filed: Feb. 24, 2017

(65) Prior Publication Data

US 2018/0247020 A1  Aug. 30, 2018

(51) Int. Cl.

| | | |
|---|---|---|
| G16H 10/60 | (2018.01) | |
| G06N 20/00 | (2019.01) | |
| A61B 8/08 | (2006.01) | |
| G06N 20/20 | (2019.01) | |
| G16H 50/20 | (2018.01) | |
| G16H 30/40 | (2018.01) | |
| G16H 50/30 | (2018.01) | |
| G06F 19/00 | (2018.01) | |
| G16H 50/50 | (2018.01) | |
| A61B 5/107 | (2006.01) | |

(52) U.S. Cl.
CPC .......... *G16H 10/60* (2018.01); *A61B 8/0875* (2013.01); *A61B 8/5223* (2013.01); *G06F 19/321* (2013.01); *G06N 20/00* (2019.01); *G06N 20/20* (2019.01); *G16H 30/40* (2018.01); *G16H 50/20* (2018.01); *G16H 50/30* (2018.01); *A61B 5/1072* (2013.01); *G16H 50/50* (2018.01)

(58) Field of Classification Search
USPC ....................................................... 382/128
See application file for complete search history.

(56) References Cited

U.S. PATENT DOCUMENTS

| | | | | |
|---|---|---|---|---|
| 6,385,283 | B1 * | 5/2002 | Stein | A61B 6/482 |
| | | | | 378/174 |
| 7,556,045 | B1 * | 7/2009 | Recknor | G16H 10/20 |
| | | | | 128/898 |
| 8,634,629 | B2 * | 1/2014 | Wilson | A61B 6/466 |
| | | | | 382/132 |

(Continued)

OTHER PUBLICATIONS

Bonaretti et al., 2014, Bonaretti S, Seiler C, Boichon C, Reyes M, Büchler P., "Image-based vs. mesh-based statistical appearance models of the human femur: Implications for finite element simulations", Med Eng Phys 2014;36:1626-35, doi:10.1016/j.medengphy.2014.09.006.

(Continued)

*Primary Examiner* — Ishrat I Sherali

(57) ABSTRACT

A computer-implemented method for personalized assessment of a subject's bone health includes extracting a plurality of features of interest from non-invasive subject data, medical images of the subject, and subject-specific bone turnover marker values. A surrogate model and the plurality of features of interest are used to predict one or more subject-specific measures of interest related to bone health. Then, a visualization of the one or more subject-specific measures of interest related to bone health is generated.

9 Claims, 18 Drawing Sheets

(56) References Cited

U.S. PATENT DOCUMENTS

2007/0274442 A1* 11/2007 Gregory ............... A61B 6/482
378/54
2010/0310141 A1 12/2010 Wilson

OTHER PUBLICATIONS

Carballido-Gamio et al., 2011, Carballido-Gamio J1, Folkesson J, Karampinos DC, Baum T, Link TM, Majumdar S, Krug R, "Generation of an atlas of the proximal femur and its application to trabecular bone analysis", Magn Reson Med. Oct. 2011;66(4):1181-91. doi: 10.1002/mrm.22885.
Heimann et al., 2009, Heimann T, Meinzer H-P., "Statistical shape models for 3D medical image segmentation: a review", Med Image Anal 2009;13:543-63. doi:10.1016/j.media.2009.05.004.
Kanis, 2002, Kanis JA., "Diagnosis of osteoporosis and assessment of fracture risk", Lancet 2002; 359(9321):1929-1936.
Poelert et al., 2013, Poelert, S., Valstar, E., Weinans, H., Zadpoor, A.A., 2013, "Patient-specific finite element modeling of bones", J. Eng. Med. 227, 464-478.
Taghizadeh et al., 2015, E Taghizadeh, M Kistler, P Büchler, M Reyes (2015), "Fast Prediction of Femoral Biomechanics Using Supervised Machine Learning and Statistical Shape Modeling in: Computational Biomechanics for Medicine", X 115-127 Springer Verlag.
Trabelsi et al., 2011, Trabelsi N, Yosibash Z, Wutte C, Augat P, Eberle S, "Patient-specific finite element analysis of the human femur—a double-blinded biomechanical validation", J Biomech. Jun. 3, 2011;44(9):1666-72.
Zadpoor et al., 2013, Zadpoor, A.A., Campoli, G.,Weinans, H., 2013. Neural network prediction of load from the morphology of trabecular bone. Appl. Math. Model. 37, 5260-5276.

* cited by examiner

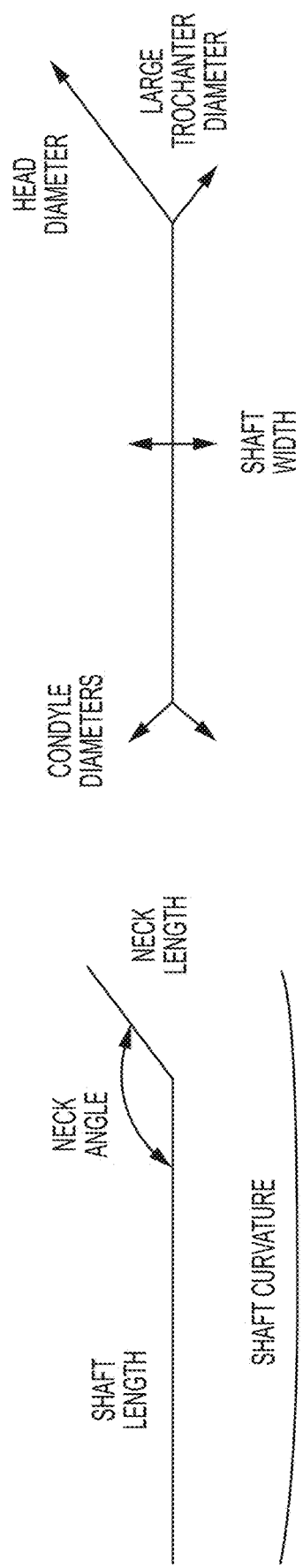
FIG. 7A
FIG. 7B
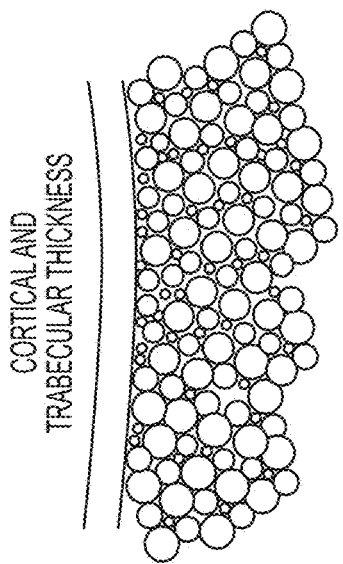
FIG. 7C

|  | FRACTURE | NON-FRACTURE |
|---|---|---|
| POSITIVE | 312 (TP) | 99 (FP) |
| NEGATIVE | 66 (FN) | 949 (TN) |

FEM — ML

THE CORRESPONDING DIAGNOSTIC STATISTICS WERE:
- ACCURACY: 88.4%
- SENSITIVITY: 82.5%
- SPECIFICITY: 90.5%
- POSITIVE PREDICTIVE VALUE: 75.9%
- NEGATIVE PREDICTIVE VALUE: 93.4%

FIG. 17

PERSONALIZED ASSESSMENT OF BONE HEALTH

TECHNOLOGY FIELD

The present invention relates generally to methods, systems, and apparatuses for personalized assessment of bone health. The disclosed techniques may be applied, for example, predicting measures of interest related to osteoporosis such as existence/severity of osteoporosis/osteopenia; fracture risk; and biomechanical characteristic of interest.

BACKGROUND

Osteoporosis is a skeletal disorder which leads to bone mass loss and diminished bone strength (as characterized by density and quality), and hence to an increased fracture risk. Bone loss typically appears due to a deficiency of estrogen in postmenopausal women, or due to other age related mechanisms (e.g. secondary hyperparathyroidism, reduced mechanical loading, etc.). Since effective drug therapies are available, it is crucial to correctly diagnose the onset of osteoporosis so as to minimize the future risk of fractures.

Approximately 22.1% of the female population, and 6.6% of the male population older than 50, are affected by osteoporosis and the percentages increase with age. Of the bone fractures caused by osteoporosis, the hip fractures are typically the most devastating ones for both the patient and society: the vast majority of patients require hospitalization and surgery. Literature reports have shown that in case of hip fractures the mortality rate increases in the first year by 8-36%. Specifically, 20% of the patients die within one year, whereas another 20% require permanent nursing home care.

A total of 3.7 million osteoporotic fractures were estimated in 2000, whereas approx. 24% represented hip fractures. Crucially, healthcare costs were estimated at a level of €36.2 billion, whereas hip fractures caused two-thirds of the expenses. Furthermore, osteoporosis related healthcare costs are expected to more than double to around €76 billion by 2050, since the estimated number of hip fractures alone is expected to increase to 6.3 million by 2050. Typically, vertebral fractures lead to fewer complications, but they are also more frequent, and previous clinical data suggests that only around 30% of them are diagnosed. Importantly, once a patient suffers a vertebral fracture, the risk for subsequent fractures increases tenfold. Besides hip and vertebral fractures, wrist fractures are the most common osteoporotic fractures, but since osteoporosis is a condition which affects the entire skeleton there is an increased fracture risk for almost any bone in the human body.

Furthermore, it has been shown that women with osteoporosis suffer a 4% decrease in bone strength per year. Thus, as mentioned above, the fracture risk increases with age, an aspect which is amplified by the age-related increase in the risk of falling. A longitudinal study was performed based on volumetric quantitative computed tomography and finite element analysis to determine the changes in bone strength. Both normal load conditions and fall related load conditions were considered. Over an average interval of five years aBMD decreased by 4%, and bone strength decreased by 4% to 12%, depending on the gender and the load conditions (more pronounced decrease for women and for fall related load conditions).

Bone is a living material which can regenerate, and whose structure and density are adapted as a result of the mechanical forces acting on it. Specifically, the bone architecture is optimized so as to resist forces with the smallest possible amount of material.

Two important characteristics when describing the mechanics of bone under loading conditions are strain (describing the deformation of the bone in comparison to its initial state) and stress (describing the internal forces of the bone). Depending on the values of these two quantities, the bone is in the pre-yield, post-yield, or ultimate state. In the pre-yield state, deformations are purely elastic; that is, any deformation is temporary and the initial state of the bone is reached once the load is removed. The most important material property for this state is the Young's modulus (stiffness or modulus of elasticity). It is the slope of the stress-strain curve, and represents the pressure which is required to act upon a bone to obtain a certain deformation. Once the yield point is surpassed, elastic deformation becomes plastic deformation, and permanent deformations are the result. The yield point is characterized by yield strain, yield stress and yield strength. Bone toughness is also used sometimes and it represents the total energy which the bone can absorb before it passes the yield point. The ultimate state is described by the ultimate strain, the ultimate stress and the ultimate strength.

Bone material is encountered in the human body either as cortical/compact bone or as cancellous/trabecular bone. On average, 80% of the bone mass is cortical and these regions of the bone ensure its stability. Cancellous bone typically resides inside of a frame formed of cortical bone and has a sponge like appearance. Its density is much smaller than that of cortical bone.

Routine clinical workflows for evaluating the risk of fracture currently rely on dual-energy X-ray absorptiometry (DXA). The main quantity extracted from DXA is the areal bone mineral density (aBMD), which was linked to an increased risk of hip fracture. However, BMD is only one facet responsible for increased fragility. Studies have shown that decreased Bone Mineral Density (BMD) determined by DXA, independent of ethnic background, sex, or age is related to an increased risk of hip fracture. DXA however has a series of disadvantages. For example, because it is two-dimensional, DXA cannot properly distinguish differential changes of cortical and cancellous bone. It has been shown that in case of many osteoporotic fractures the bone was not characterized as being osteoporotic by the DXA scan. Specifically, the sensitivity of DXA-based decision making is too low. Bone mineral content (BMC) is sometimes used as an alternative to BMD.

Recent research has demonstrated that biomechanical modeling techniques, based on finite element analysis (FEA), bear great potential of improving clinical decision making processes. These techniques combine geometrical information extracted from medical imaging (structural properties, anatomical shape) with background knowledge on the patient (e.g., demographics) and patient-specific information (e.g. loads), encoded in a complex mathematical solid mechanics model consisting of partial differential equations which can be solved only numerically. This approach leads to a large number of algebraic equations, making it computationally very demanding. Typically, the solution of these models requires a time frame from a few minutes to a few hours for high-fidelity models representing the complete three dimensional space.

Since the FEA analysis is typically based on CT imaging data, it is sometimes also called biomechanical CT (BCT). When performing BCT, the gray-scale voxels in the CT DICOM image are converted to calibrated values of BMD.

Bone is segmented from the data and used to create a finite element model (FEM). By applying an FEM solver, a stress analysis may be performed to determine measures of interest related to the strength of the bone. Several measures of interest may be derived from such an analysis including whole-bone strength, load-to-strength ratio, the type of fracture, average stress, average strain, and stiffness.

In-vitro studies performed on cadaver bones have demonstrated that BCT provides superior estimates of vertebral and femoral bone strength, as compared to DXA-based aBMD. Patient-specific FEA was performed for 12 cadaver femur bones in a double blinded fashion by two different research groups to determine numerical errors but also errors with respect to experimental findings, as determined from in-vitro experiments. Numerical results indicated the computations are robust and match well experimental findings.

In one of the first clinical studies it was shown that vertebral strength, as assessed by the stress, is superior compared to BMD for the assessment of osteoporotic fracture risk. More recently the utility of BCT was confirmed in a patient cohort for which aBMD was not able to differentiate between patients with and without fractures. This finding was also confirmed in a study focused on the femur bone.

It has been concluded that FEMs can predict femoral fracture loads more accurately than other methods. On the other hand, FEA accuracy depends on the modeling methodology, and requires further standardization.

Since during an FEA simulation the strain may increase beyond the yield strain of the bone material, typically a von Mises strain criterion is employed: a small Young's modulus (e.g., 0.01 MPa), is assigned to all finite elements which have a strain larger than the yield strain.

A retrospective study on 1110 individuals, which employed an FEA based assessment of bone strength, indicated that fracture prediction can be performed for women by combining femoral strength with femoral neck areal BMD.

The effect of scanner settings on FEA results was recently evaluated in a study on cadaver bones: both low and high resolution scanner settings were considered. Strength and stiffness values estimated from data acquired with the two imaging setups differed, indicating that the robustness of this method needs to be increased.

In a very recent study, digital volume correlation analysis of micro-computed tomography images acquired during compression and flexion of spine segments, were used to measure displacements, which were then compared to FEA results. The computational results were able to partially capture the vertebral failure patterns, but further work is required to obtain accurate predictions of failure mechanisms from FEA.

Furthermore, BCT may be employed to gain further insight into the bone mechanics, by changing the anatomical models and/or its properties and rerunning the FEA. For example, the outer layer of the bone may be removed, to determine the variation in bone strength.

One of the disadvantages is that BCT requires a CT, which is associated with a higher cost and radiation compared to a DXA scan. However, BCT may be applied based on images acquired during previous CT scans or acquired during CT scans performed for a different scope (lung cancer screening, a cardiac CT for ruling out coronary artery disease, abdominal/pelvic region, etc.). Given the fact that millions of CT scans are performed per year, BCT bears a great potential, and would actually be more convenient than a DXA scan. Very recently it was shown that CT images acquired for colonography are suitable for performing FEA based BCT analysis, without requiring changes in the imaging protocol.

However, central quantitative CT is currently not an established imaging method for diagnosing patients based on BMD as being osteopenic or osteoporotic. Nevertheless, volumetric exclusively cancellous BMD may be employed to assess therapies. Currently, quantitative CT is recommended as an alternative to DXA if: (i) the individual is very large or very small, (ii) the individual is expected to have advanced degenerative disease in the lumbar spine, and (iii) monitoring of metabolic bone change is required.

Importantly, the clinical potential of BCT analysis for spine and hip has been recently acknowledged by the International Society of Clinical Densitometry. It has been noted that the usage of BCT in routine clinical practice still has to overcome a few challenges related to the availability of FEA software and integration in the clinical workflow. As described above, a significant opportunity is the secondary use of CT scans for the assessment of risk of fracture and osteoporosis diagnosis (use CT scans performed originally for the chest, abdominal and pelvic regions). Alternatively, it has been shown that 3-T MRI of femur microarchitecture can also be used to assess the strength of a bone based on FEA. The major disadvantage of FEA is that at least a few hours are required to perform a detailed analysis, which may represent a too large timeframe for a routine clinical workflow.

The World Health Organization (WHO) has introduced Fracture Risk Assessment Tool (FRAX) as a diagnostic tool to estimate the risk of bone fracture over a 10 year time span. FRAX is based on BMD assessed at the femoral neck and estimated fracture probabilities for the hip or for other osteoporosis relevant locations (spine, forearm, shoulder). This tool further incorporates information related to age, ethnicity, sex, weight, height, fracture history, smoking, alcohol, glucocorticoids, and rheumatoid arthritis. The accuracy of the FRAX score has been shown to be limited, with an area under the curve (AUC) of 0.56 to 0.69.

Before FRAX, a grading system was developed specifically for osteoporotic vertebral fractures, which, amongst others, is recommended by ISCD, the International Osteoporosis Foundation, and the European Society of Skeletal Radiology. This system defines a vertebral fracture as a vertical deformation of more than 20% and a reduction of the height area of 10-20%, and three different fracture grades are defined (mild, moderate and severe). The approach was tested in several clinical studies.

One alternative proposed in literature is 3D statistical shape and appearance modeling. It uses a database of 3D bone images and is based on the average shape and density distribution and their main modes of variation. To determine the shape and density of a new patient-specific bone, one only needs to determine the contribution of the main modes to the shape and distribution of the current bone. Thus a 2D image, as acquired through DXA may be used, followed by a 2D-3D matching algorithm which outputs the weights of the contributions. This methodology circumvents the usage of Quantitative Computed Tomography (QCT) and image segmentation. An FEA analysis may be performed based on the resulting 3D model.

Recently, a methodology based on machine learning (ML) was employed to predict measures of interest extracted from FEA (i.e. stress). A database of 89 femur bones was used, and features were based on a statistical shape model, and morphometric and density information. The distribution of stress was predicted with a correlation of 0.98.

Another important application for DXA/BCT in the context of bone material analysis is the early evaluation of drug-based treatment in terms of their efficiency, especially in women with osteoporosis. As in the case of risk of fracture evaluation, aBMD is not able to comprehensively assess the efficiency of a drug-based treatment and BCT has shown to provide superior discriminatory power. BCT leads to increased statistical power and improved insight into the treatment effect.

One reason for the discrepancies between aBMD and BCT is that for some treatment plans the cortical bone density increased while the trabecular bone density decreased, leading to an overall approximately constant aBMD value. From a biomechanical point of view, however, the bone strength increased in these cases.

One possible drug treatment for osteoporotic patients employs teriparatide: the trabecular bone volume is increased, thus improving the structure of the bone, and also the thickness of the cortical layer is increased. Alendronate is another drug used to treat osteoporotic patients: a study has shown that it leads to similar improvements in femoral strength as teriparatide. In another recent study it was shown that teriparatide increased both vertebral and femoral strength, as assessed by FEA performed based on quantitative CT scans.

BCT may also be used to assess the effect of changes in treatment plans. Previous studies have shown that in case of treatment plans based on alendronate or raloxifene, the addition or the switch to teriparatide lead to different outcomes as assessed by aBMD. In a recent study, BCT was employed to further evaluate these two strategies and to additionally also compute vBMD (volumetric BMD) from quantitative CT. It was shown that in women with osteoporosis the addition and the switch to teriparatide lead to similar outcomes for the spine strength. Regarding the hip strength, it increased more in the group of teriparatide addition.

In another study, a different drug treatment plan based on denosumab was evaluated using BCT analysis. It was shown that the strength of both trabecular and cortical bone improved in time as assessed through FEA.

Romosozumab is yet another drug used for patients with high risk of bone fracture: it boosts bone formation and inhibits bone resorption. Linear FEA was recently employed to assess the bone stiffness in a longitudinal study of a treatment plan based on Romosozumab: the whole bone stiffness increased significantly and rapidly after three months of drug administration.

Over the last years, biomarkers have received increased attention for the assessment of bone strength and fracture risk. Typically these markers are called bone turnover markers (BTM). These are based on the evaluation of proteins and enzymes which are generated during processes of bone formation and bone resorption. Typically used markers of bone formation include serum total alkaline phosphatase, serum bone-specific alkaline phosphatase, serum osteocalcin, and serum type 1 procollagen (C-terminal/N-terminal). Typically used markers of bone resorption are urinary hydroxyproline, urinary total pyridinoline (PYD), urinary free deoxypyridinoline (DPD), urinary collagen type 1 cross-linked N-telopeptide (NTX), urinary or serum collagen type 1 cross-linked C-telopeptide (CTX), bone sialoprotein (BSP), and tartrate-resistant acid phosphatase 5b.

BMTs are currently not used routinely in the assessment of osteoporosis; however several studies have shown that the average values of these markers differ between groups of osteoporotic patients and healthy subjects. Furthermore, it has been shown the biomarkers may also be used to assess the bone strength: a recent study validated the biomarker P1NP (amino-terminal-propeptide of type I collagen) as a good predictor of bone strength, as determined from FEA.

Other measures to be used as biomarkers may be extracted from different imaging techniques, like ultrasound: broadband ultrasound attenuation (BUA), speed of sound (SOS), and the resulting stiffness value and quantitative ultrasonometry (QUS) index.

In conclusion, three different categories of markers have shown to be linked to the risk of bone fracture: BMD (areal, volumetric, etc.), FEA based markers, and BTM.

SUMMARY

Embodiments of the present invention address and overcome one or more of the above shortcomings and drawbacks, by providing methods, systems, and apparatuses related to a personalized assessment of bone health. More specifically, the techniques described herein utilize ML algorithms for predicting measures of interest to bone health (whole-bone strength, load-to-strength ratio, the type of fracture to be expected, local/average stress, local/average strain, local/global stiffness; effect of a drug-treatment, e.g. increase in bone strength in time; disease evolution, e.g. decrease in bone strength in time, etc.). The prediction is based on various features extracted from non-invasive patient data, medical imaging (invasive and non-invasive, perfusion), invasive measurements, blood biomarkers, etc. Furthermore, the disclosed techniques may also be applied to the prediction of risk of future events.

According to some embodiments, a computer-implemented method for personalized assessment of a subject's bone health includes extracting features of interest from non-invasive subject data, medical images of the subject, and subject-specific bone turnover marker values. A surrogate model and the features of interest are used to predict one or more subject-specific measures of interest related to bone health. Then, a visualization of the one or more subject-specific measures of interest related to bone health is generated.

Some embodiments of the aforementioned method further includes retrieving training data comprising one or more of (i) bone anatomical models and (ii) in-vitro models from a database and performing FEM-based computations using the bone anatomical models or stress-experiments using the in-vitro models to yield FEM results. Next, measures of interest are extracted from the FEM results and geometric features are extracted from the bone anatomical models. The surrogate model is trained to predict the one or more measures of interest based on the geometric features using a machine learning algorithm. In one embodiment, the measures of interest comprise one or more of stress and stress strain. In other another embodiment, at least a portion of the training data comprises synthetic data. This synthetic data may be generated, for example, by generating one or more baseline models and randomly or systematically perturbing the baseline models to obtain synthetic models comprising one or more of (i) synthetic bone anatomical models and (ii) synthetic in-vitro models. In one embodiment, these baseline models are subject-specific anatomical models. In one embodiment, the synthetic data comprises one or more of (i) synthetic bone anatomical models and (ii) synthetic in-vitro models generated according to a set of rules using one or more randomly or systematically perturbed parameter values.

In some embodiments of the aforementioned method, each of the one or more subject-specific measures of interest is associated with a point on a subject image. The subject image is displayed and, in response to receive a user selection of a selected point on the subject image, a particular subject-specific measure of interest corresponding to the selected point is displayed. In some embodiments, each of the one or more subject-specific measures of interest with a point on a subject image. Then, an image color coded based on values of the subject-specific measures of interest is displayed.

According to other aspects of the present invention, a second computer-implemented method for personalized assessment of a subject's bone health includes extracting subject-specific geometry data from medical images and geometric features of a bone anatomical model based on the subject-specific geometry data. One or more first machine learning models are used to predict one or more subject-specific biomechanical characteristics of interest based on the geometric features of the bone anatomical model. Subject-specific features are extracted from additional subject measurement data. Then, the second machine learning models and the subject-specific features are used to (i) predict subject-specific measures of interest related to bone health; (ii) adapt the subject-specific biomechanical characteristics of interest; or (iii) predict an effect of a treatment plan related to bone health.

Various enhancements, refinements, or other modifications may be made to the aforementioned second method in different embodiments of the present invention. For example, in one embodiment, the subject-specific features comprise one or more of age, ethnicity, sex, weight, height, fracture history, family history, smoking, alcohol, glucocorticoids, and rheumatoid arthritis, aBMD, vBMD, bone turnover markers, and ultrasound based measurements. In another embodiment, the first machine learning models are trained on synthetic data. The second machine learning models may be further trained to predict the effect of the treatment plan related to bone health based on subject-specific features and longitudinal data related to treatment plan effects. For example, in one embodiment, the effect of the treatment plan comprises effects corresponding to different treatment drugs, different combinations of treatment drugs, changes in treatment plans, and/or effects specific to subjects that have previously suffered one or more fractures.

According to other embodiments of the present invention, a parallel processing computing system includes a host computer configured to extract features of interest from non-invasive subject data, medical images of a subject, and subject-specific bone turnover marker values. The system further includes a device computer configured to use a surrogate model and the features of interest to predict one or more subject-specific measures of interest related to bone health.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 7A illustrates the first step of a three-step method for generating two-dimensional synthetic femur anatomical models, according to some embodiments;

FIG. 7B illustrates the second step of a three-step method for generating two-dimensional synthetic femur anatomical models, according to some embodiments;

FIG. 7C illustrates the third step of a three-step method for generating two-dimensional synthetic femur anatomical models, according to some embodiments;

FIG. 17 depicts a confusion matrix and corresponding diagnostics statistics gathered using the techniques described herein.

DETAILED DESCRIPTION OF ILLUSTRATIVE EMBODIMENTS

The following disclosure describes the present invention according to several embodiments directed at methods, systems, and apparatuses related to personalized assessment of bone health. This technology is described herein with examples directed at osteoporosis; however, it should be understood that the disclosed techniques may be generally be applied to the assessment of other bone health conditions as well.

The techniques described herein refer to the usage of machine learning (ML) algorithms for predicting measures of interest related to osteoporosis: existence/severity of osteoporosis/osteopenia; fracture risk (score, percentage); biomechanical characteristic of interest, as extracted typically from finite element analyses: whole-bone strength, load-to-strength ratio, the type of fracture to be expected, local/average stress, local/average strain, local/global stiffness; effect of a drug-treatment, e.g. increase in bone strength in time; disease evolution, e.g. decrease in bone strength in time. The prediction may be based on various features extracted from non-invasive patient data, medical imaging data (DXA, CT, MRI, etc.), and bone turnover markers. One major advantage of the proposed ML-based workflows is that data from heterogeneous sources may be integrated to perform a comprehensive assessment. The techniques described herein may also use imaging data acquired previously for a different scope (e.g., CT scans: lung cancer screening, a cardiac CT for ruling out coronary artery disease, abdominal/pelvic region, etc.); that is, they provide the opportunity for a secondary use of scans for the assessment of risk of fracture and osteoporosis diagnosis. Furthermore, the online prediction phase is extremely fast, it outputs results in near real-time, and can be run directly on a workstation on-site.

Figure 1:
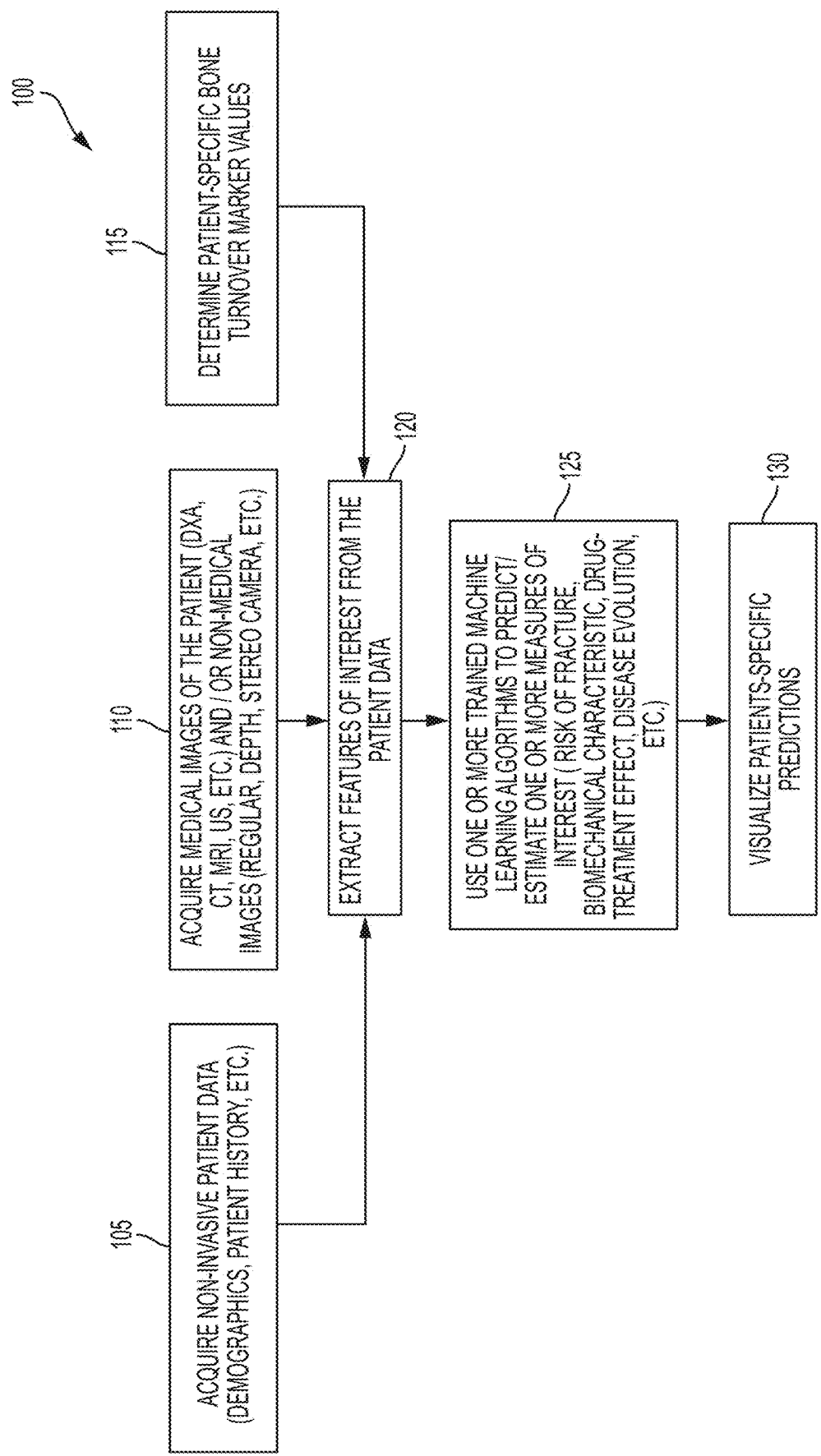
FIG. 1 illustrates a generic workflow used to predict measures of interest for patients with osteoporosis, according to some embodiments.

FIG. 1 displays a generic workflow 100 that may be used for predicting measures of interest for patients with osteoporosis, according to some embodiments. The central element of the workflow is represented by one or more trained ML algorithms which use a set of features for the prediction. This workflow is described below as a series of steps; however, it should be understood that order should not be implied by the description of these steps. For example, acquisition steps 105-115 could be performed in any order and multiple acquisition steps may be performed in parallel.

At step 105, non-invasive patient data is received such as, for example, demographics and patient history (e.g., age, ethnicity, sex, weight, height, fracture history, family history, smoking, alcohol, glucocorticoids, rheumatoid arthritis, etc.). Even if BMD is in the range of normal values, low-impact fragility fractures can represent a significant indicator for osteoporosis. Non-invasive/invasive medical images of the patient are received at step 110. These images may generally be received from any source including, for example, DXA, CT, MRI, and/or Ultrasound. Non-medical imaging data is also received at step 110 including, without limitation, regular, stereo, depth, range imaging, etc. This data may be used to assess external features of the patient, like the posture (during stand-still) or the gait (during walking or running).

At step 115, patient-specific bone turnover markers value are received. These markers may include, without limitation, serum total alkaline phosphatase, serum bone-specific alkaline phosphatase, serum osteocalcin, serum type 1 procollagen (C-terminal/N-terminal): C1NP or P1NP, urinary hydroxyproline, urinary total pyridinoline (PYD), urinary free deoxypyridinoline (DPD), urinary collagen type 1 cross-linked N-telopeptide (NTX), urinary or serum collagen type 1 cross-linked C-telopeptide (CTX), bone sialoprotein (BSP), tartrate-resistant acid phosphatase 5b.

The information acquired at steps 105-115 may be acquired at a single time point, or at different time points. For example, features extracted from a DXS scan performed several months before a fracture event, and a CT exam performed right after the fracture event may be used to predict the measure of interest. Similarly, bone turnover biomarkers (the same or different) may have been acquired at different time points and used as features of the ML algorithm.

At step 120, features of interest are extracted from the patient data acquired at steps 105-115, for example, using feature extraction techniques generally known in the art. The term "extraction," as used herein refers to the act or process of retrieving data out of one or more data sources for further processing or storage. The act of extracting data may include the identification of data in a data source. For example, during extraction relevant features from an image may be identified and retrieved from the data (e.g., by cropping). Alternatively, a feature extraction process may take such an identification as input and only perform the steps associated with retrieval.

Returning to FIG. 1, at step 125, one or more trained ML algorithms are used to predict/estimate one or more measures of interest including, without limitation, existence/severity of osteoporosis/osteopenia; fracture risk (score, percentile, etc.); biomechanical characteristic of interest, as extracted typically from FEA: whole-bone strength, load-to-strength ratio, the type of fracture to be expected, local/average stress, local/average strain, local/global stiffness; effect of a drug-treatment (e.g. increase in bone strength in time); and disease evolution (e.g. decrease in bone strength in time). The one or more ML algorithms may be used in a cascaded or parallel workflow, and may be trained on patient-specific and/or on synthetic data, generated in vitro or in silico. In general, any ML algorithm known in the art may be applied including, for example, algorithms based on artificial neural networks (ANN), deep learning, or learning classifier/regression systems.

Continuing with reference to FIG. 1, at step 130, patient-specific predictions are visualized based on the output of the ML algorithms. For example, in some embodiments, the data is presented in a numeric (e.g. tabular) form to the clinician. In other embodiments, the data is presented in a graphical way (e.g., overlaid on the medical images) and presented to the clinician.

The ML-based workflows shown in FIG. 1 provide several advantages in conventional osteoporosis assessment techniques. For example, data from heterogeneous sources may be integrated to perform a comprehensive assessment. Additionally, these techniques may use imaging data acquired previously for a different scope (e.g., CT scans: lung cancer screening, a cardiac CT for ruling out coronary artery disease, abdominal/pelvic region, etc.). That is, the techniques provide the opportunity for a secondary use of scans for the assessment of risk of fracture and osteoporosis diagnosis. Moreover, the online prediction phase can be implemented using architectures that are extremely fast, outputting results in near real-time. As a result, these algorithms may be run directly on a workstation on-site.

Figure 2:
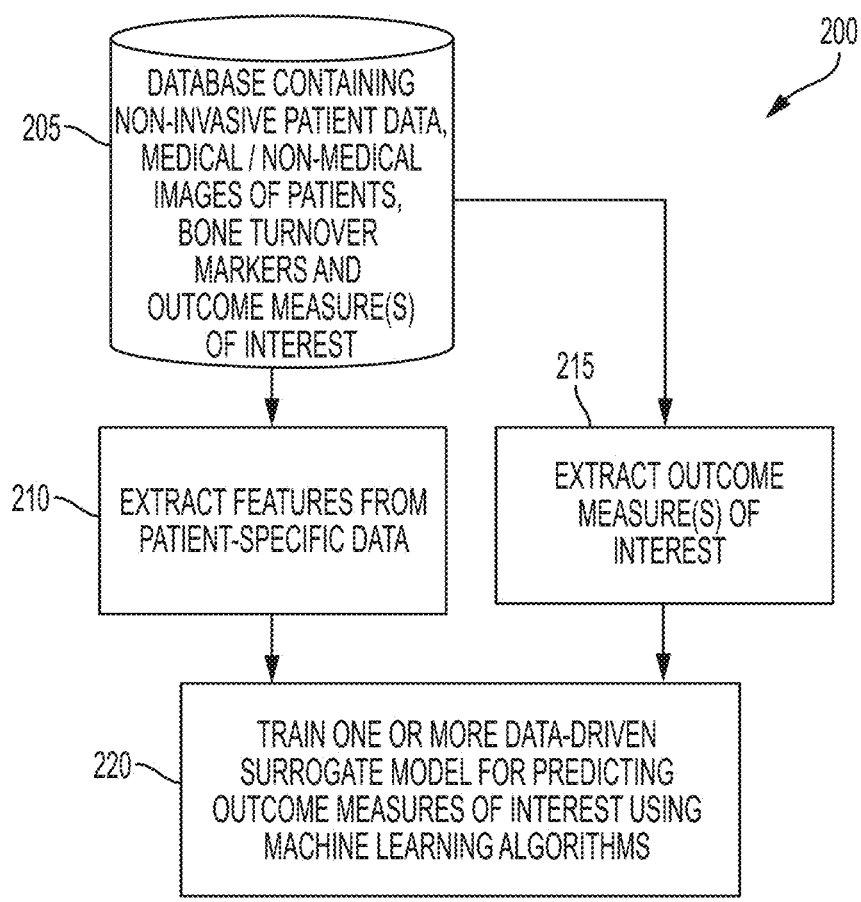
FIG. 2 depicts a generic workflow used to train one or more data-driven surrogate models for predict measures of interest for patients with osteoporosis, according to some embodiments.

The workflow displayed in FIG. 1 is used during the prediction phase which is performed online. To be able to use one or more machine learning algorithms these have to be trained a priori offline. FIG. 2 displays a generic workflow of the training phase, as it may be applied in some embodiments. The most important aspect for the training phase is the existence of a large database 205 comprising patient-specific information (non-invasive data, medical images, bone turnover markers) and patient-specific outcome measures of interest for osteoporosis (e.g., fracture occurrence, fracture severity, quantity extracted from a biomechanical FEA, etc.). Once this database is established, at steps 210 and 215, features are extracted from patient-specific data and outcome measures of interest are extracted. Then, at step 220, the extracted data is used to train a data-driven surrogate model for predicting the outcome measures of interest using ML algorithms.

During the training phase more features may be available than during the online prediction phase. The features which are missing during the prediction phase may be estimated based on similar datasets in the training database, (e.g., by employing a separate machine learning algorithm specifically trained for this purpose).

Figure 3:
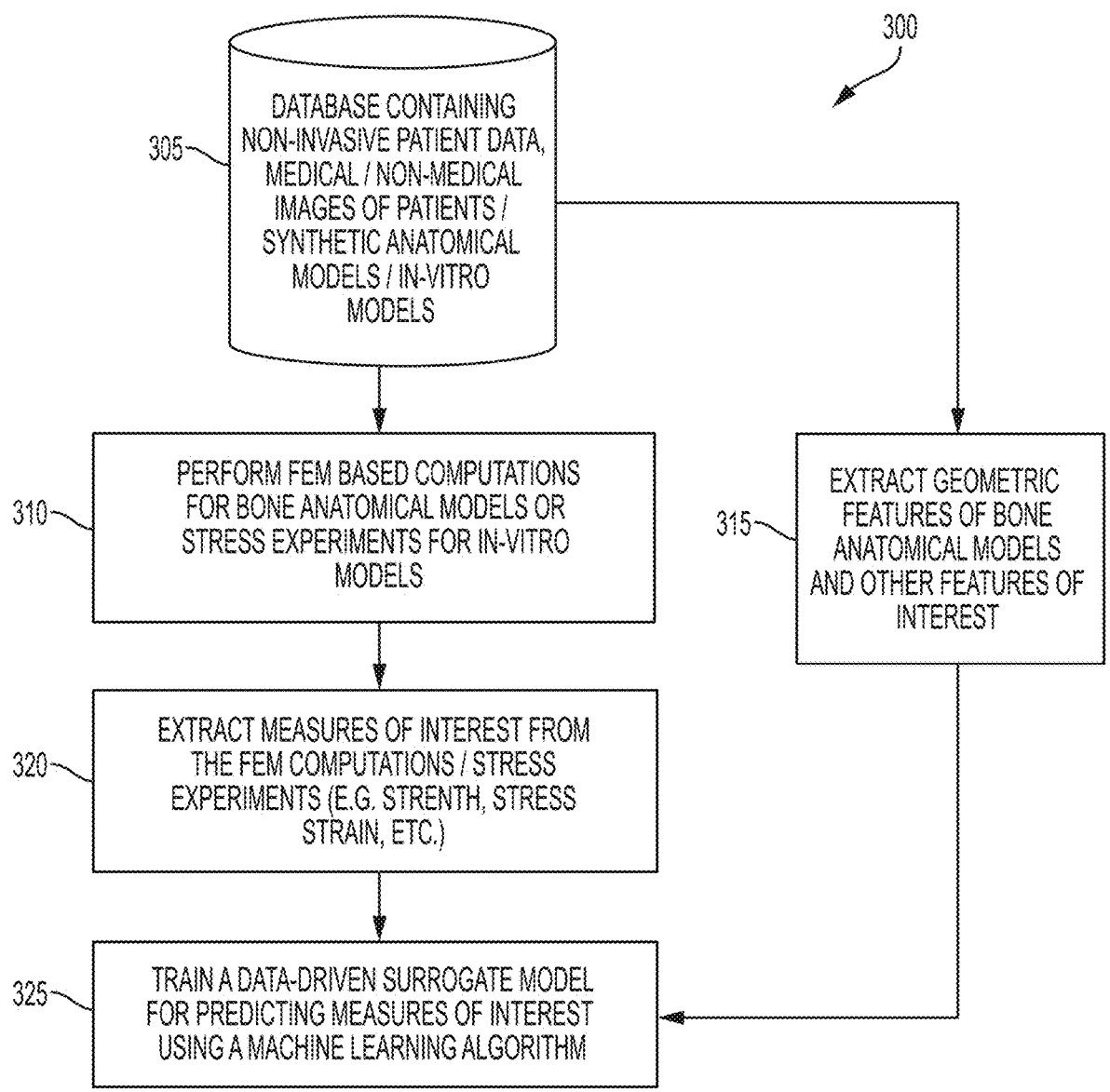
FIG. 3 shows a workflow used to train one or more data-driven surrogate models for predicting biomechanical characteristics of interest, according to some embodiments.

FIG. 3 illustrates an example use case for which the measure of interest to be predicted by the machine learning model is a biomechanical characteristic as determined from an FEM based simulation or an in-vitro experiment. At step 310 FEM-based computations for bone anatomical models or stress experiments are performed for in-vitro models based on data from database 305. At step 315 (performed before, during, or after step 310), geometric features of bone anatomical models or other features of interest are extracted using data from the database 305.

At step 320, measures of interest are extracted from the FEM computations/stress experiments. The measure of interest may be, for example, whole-bone strength, load-to-strength ratio, average/local stress, average/local strain, stiffness, etc. Besides the medical images, also non-invasive patient data is employed, since this type of information is used to generate the boundary conditions for the FEM simulation/loading conditions for the in-silico/in-vitro experiments (e.g., the weight of the patient), and is therefore also required in the feature vector. Then, at step 325, a data-drive surrogate model is trained for predicting measures of interest using the information from steps 310-320.

In case the workflow is based on FEM simulations, the anatomical bone models may be generated from medical images acquired from patients. Alternatively, synthetic anatomical models may be generated and the corresponding non-invasive data like associated weight may be generated by an associated algorithm. The anatomical models may refer to a whole bone (e.g., the femur bone, or vertebrae) or only to a part of a bone (e.g., cancellous volume of a bone). The FEM simulations may be two- or three-dimensional. Alternatively, a hybrid database of synthetic and patient-specific models may be employed.

In case in vitro experiments are used to generate the training database, techniques generally known in the art may be used for performing the experiments and determining the corresponding outcome measures of interest. Also, as mentioned above, experiments may be performed with whole bones or with certain parts of the bone.

Figure 4:
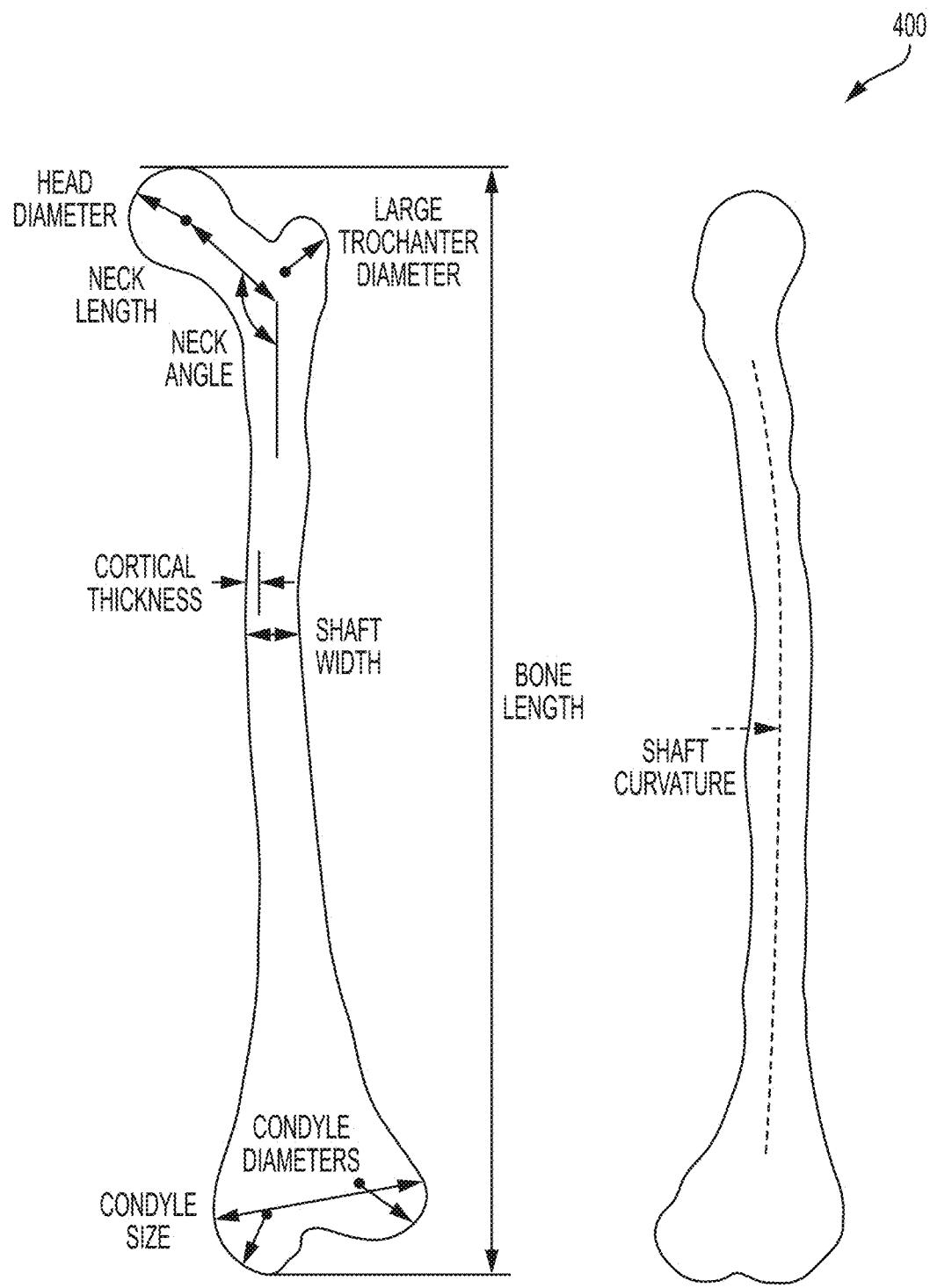
FIG. 4 illustrates femur bone morphometric features.

The features that are used to describe the anatomical model may be morphometric features which are based on various measurements of the bone. As illustrated in FIG. 4, the femur bone morphometric features for the femur bone include, without limitation, head diameter, large trochanter diameter, condyle diameter, bone length, neck length, shaft width, cortex thickness, condyle size, small trochanter position, neck angle, and shaft curve diameter. These features may be extracted from 3D data or from one or multiple 2D views, depending on the available medical imaging data. Feature extraction may be manual or automatic.

Additionally, since several bones in the human body, like the femur bone, have a slight curvature, additional features may be defined to describe this characteristic. For example, if the centerline of the bone is defined as a discrete curve composed of 3D points, a spline interpolation may be first performed to determine a continuous curve $C(x(t), y(t), z(t))$, with t taking values between t0 and t1. Next, the following measures are computed:

$$\text{Arc length: } arcLength(C) = \int_{t_0}^{t_1} \sqrt{x'(t)^2 + y'(t)^2 + z'(t)^2}\, dt$$

$$\text{Chord length: } chordLength(C) =$$
$$\sqrt{(x(t_1) - x(t_2))^2 + (y(t_1) - y(t_2))^2 + (z(t_1) - z(t_2))^2}$$

$$\text{Curvature: } \kappa(t) = \frac{\|r'(t) \times r''(t)\|}{\|r'(t)\|^3}, \text{ where}$$

$$r'(t) = (x'(t), y'(t), z'(t)) \text{ and } r''(t) = (x''(t), y''(t), z''(t))$$

$$\text{Total curvature: } t_c = \int_0^{arcLength} \kappa(s)ds,$$

where $s$ is the arc length variable along the curve $$\text{Total squared curvature: } t_{sc} = \int_0^{arcLength} \kappa^2(s)ds$$

Based on these measures, several features may be defined, some of which are given below:

$$\tau_0 = \frac{chordLength}{arcLength},$$

$$\tau_1 = \frac{arcLength}{chordLength} - 1,$$

$$\tau_2 = t_c,$$

$$\tau_3 = t_{sc},$$

$$\tau_4 = \frac{t_c}{arcLength},$$

$$\tau_5 = \frac{t_{sc}}{arcLength},$$

$$\tau_6 = \frac{t_c}{chordLength},$$

$$\tau_7 = \frac{t_{sc}}{chordLength}.$$

Furthermore, statistical shape and appearance modeling may be employed to extract other types of features. Advanced techniques like active shape models or hierarchical shape models may be employed in some embodiments. Only the top modes in these statistical models may be used as features, so as to cover, for example, 95% of the variation in the dataset.

Figure 5:
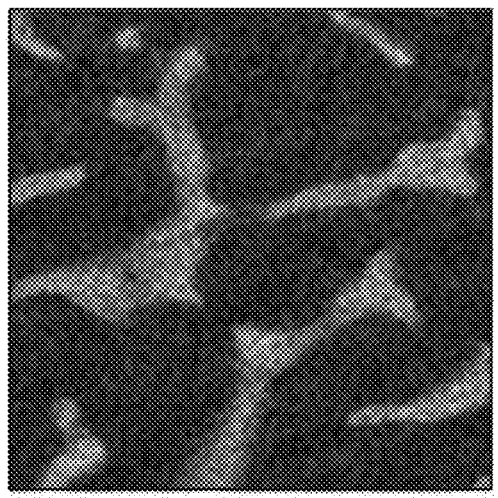
FIG. 5 depicts 3D slices of a cancellous bone segment.
Figure 5:
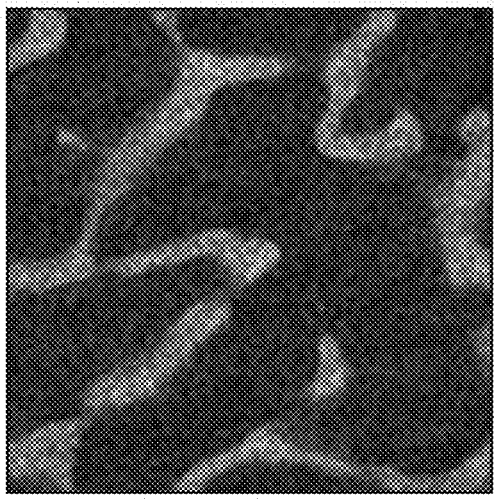
Figure 6:
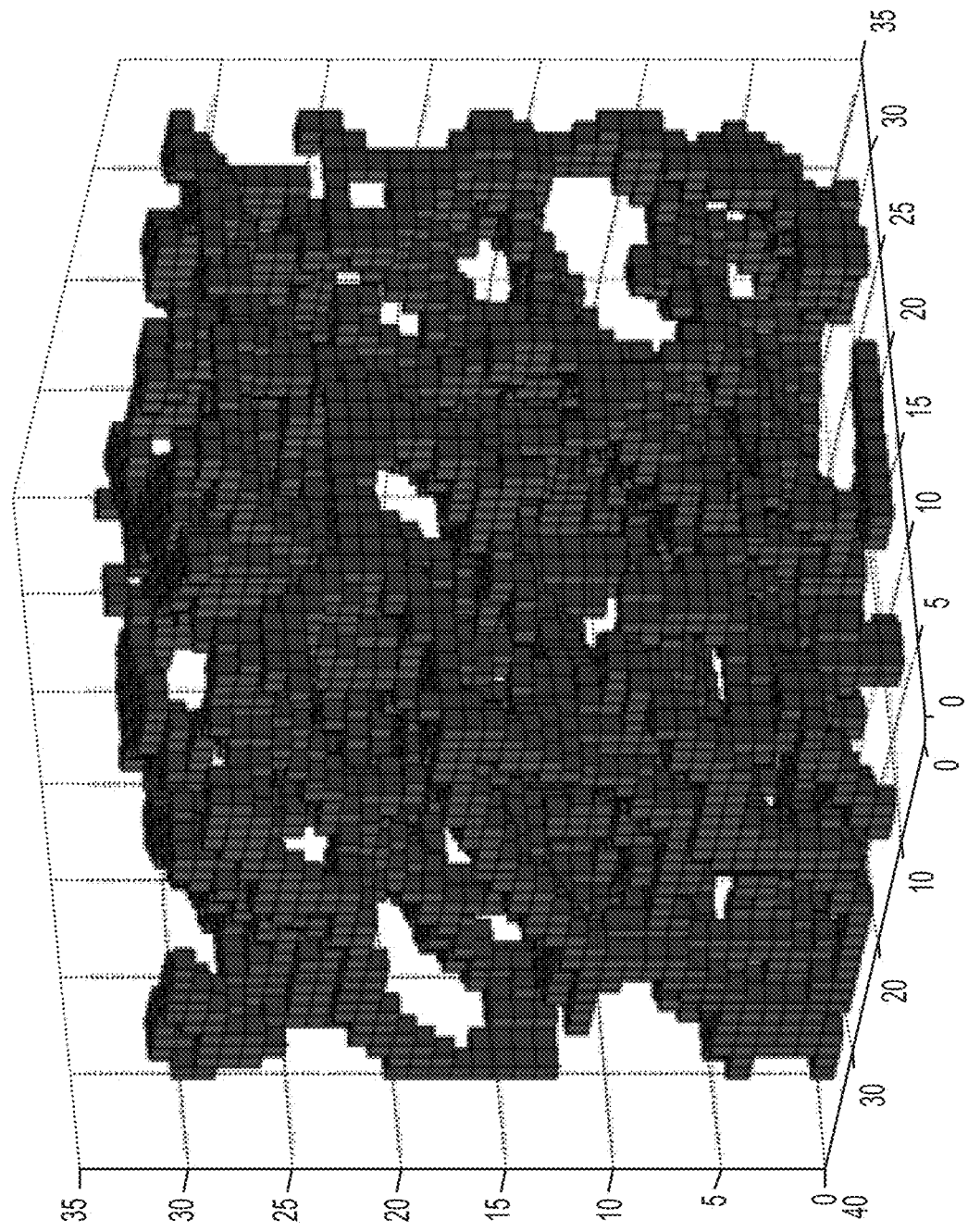
FIG. 6 shows 3D anatomical model of a cancellous bone segment.

In case only a part of a bone is analyzed, e.g. cancellous volume of a bone, other types of features need to be defined. These anatomical models may be generated for example based on micro CT data (2D slices of a cancellous bone segment as shown in FIG. 5), whereas each voxel in the original image is tagged as being either a bone voxel or an empty space (based on averaging and thresholding of voxel intensity values). After applying a series of post-processing techniques (e.g., to exclude isolated islands), a 3D model like the example shown in FIG. 6 may be obtained.

Sample features that may be used for this type of anatomical model include, without limitation, total number of bone voxels present in the binary matrix, total number of bone voxels which also have a bone voxel next to it along positive and/or negative Ox/Oy/Oz direction, total number of bone voxels which also have bone voxels next to it both for the Ox and Oy axis (along the positive and/or negative direction), total number of bone voxels which also have bone voxels next to it both for the Ox and Oz axis (along the positive and/or negative direction), total number of bone voxels which also have bone voxels next to it both for the Oy and Oz axis (along the positive and/or negative direction), and total number of bone voxels which also have bone voxels next to it on the Ox, Oy and Oz axis (along the positive and/or negative direction). These properties contain information about the voxel connectivity in the cancellous structure. Specifically, the higher the values, the better the connectivity and the more structurally solid is the anatomical model.

In some embodiments, synthetic data is used to train the ML algorithms discussed herein. The use of synthetic models instead of patient-specific models in the training database has several advantages: For example, a very large number of cases can be automatically generated, leading thus to an extensive database. Additionally, complex pathological configurations can be generated: small/large cortical thickness, small/large cancellous density, etc. Since the generation of synthetic in-silico geometries can be completely automated, the cost of generating a large database is reduced. Rare pathological cases can be sampled better and the synthetic approach can be extended to different demographic groups easily. Moreover, the training can be performed in a global manner or a site-specific manner. This allows the system to account for anatomical trends based on patient demographics and epidemiology. The training can also be iteratively improved with either more data, or with better representations of the features.

To generate a database of synthetic bone models, different approaches can be used (these in-silico models can be either three-dimensional or two-dimensional.). For example, one or more baseline models may be generated whose properties are then randomly or systematically perturbed to obtain a large number of models. If some real patient anatomical models are available, further synthetic models can be constructed by stochastically perturbing the features of the patient-specific models. Alternatively, each model may be generated separately by following a set of rules and by randomly or systematically perturbing the parameter values of these rules. In the first case, the baseline models can be represented by healthy population average bone anatomical models. In the second case scaling laws and atlases may be used for generating realistic synthetic models.

Furthermore, the generation of synthetic data may comprise generating synthetic images, similar to those obtained from different imaging modalities (DXA, CT, MRI, etc.). Also, in this case, both approaches described above may be applied (create one or more baseline images, and perturb them; or generate each image separately with a set of rules that are based on randomly generated parameters). The synthetic geometries may then be extracted from these synthetic images using the same techniques as in the case of patient-specific images.

FIGS. 7A-7C illustrates a three-step method for generating two-dimensional synthetic femur anatomical models. In the first step (shown in FIG. 7A), a one-dimensional skeleton of the femur bone is generated, by specifying the shaft length, the neck length, the neck angle, and the shaft curvature. During the second step (shown in FIG. 7B), various diameters (condyle, head and large trochantic diameters) and the shaft width are prescribed. Once the second step is complete the outer contour of the femur bone can be generated by interpolating based on these parameters. During the third step, (shown in FIG. 7C) the inside properties of the bone are determined by specifying the width of the cortical bone and of the cancellous bone at each location. By applying this three-step algorithm, an unlimited number of femur geometries may be generated.

Figure 8:
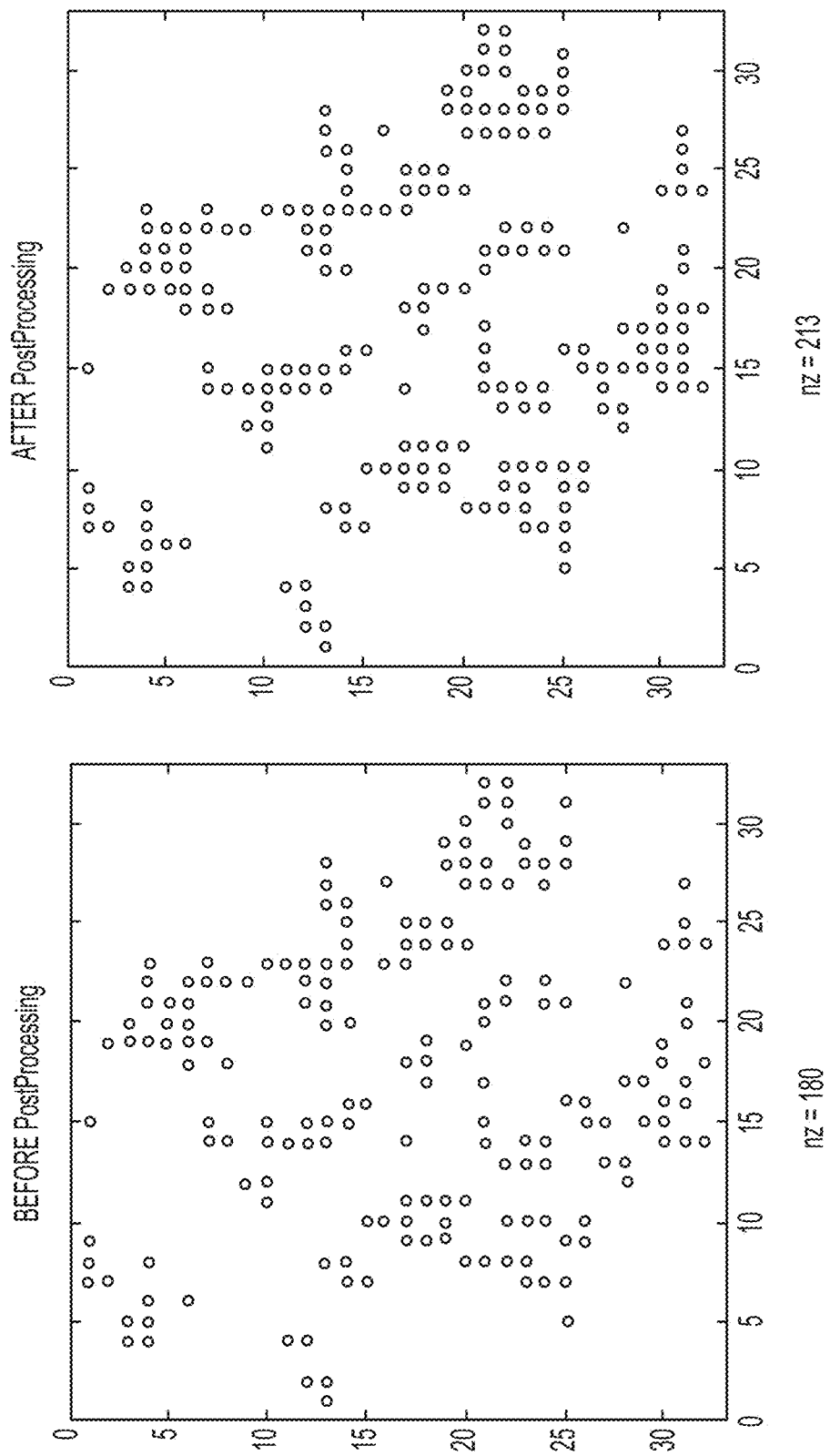
FIG. 8 depicts 2D slice of synthetic data before and after applying the post-processing algorithm, according to some embodiments.

To generate synthetic data of the type depicted in FIGS. 7A-7C, the following workflow may be selected. First, the size of the domain is chosen (number of voxels in each direction), e.g. 32×32×32. Secondly, a 3D matrix of the chosen size of uniformly distributed random numbers in the range of (0, 1) is generated. A threshold for classifying the voxels into bone voxels or empty voxels is chosen (e.g. between 0.63 and 0.67). Next, a filter is applied to remove all but the largest island of the matrix, and also to discard any poorly connected voxels. Then, post-processing is performed to improve the statistical properties of the structures so as to resemble patient-specific cancellous data. The post processing algorithm searches for certain gaps in the voxel structure and fills them. For example, if two voxels on the same line/column are separated by a gap, the corresponding voxel is turned into a bone voxel. This algorithm is applied at slice level for various plane orientations (i.e. parallel to the xOy, xOz, yOz planes) and/or on the Oz axis. The post-processing step improves the voxel connectivity. This has a positive effect on the structural robustness. FIG. 8 displays an example of a slice of the 3D matrix, before and after post-processing.

Figure 9:
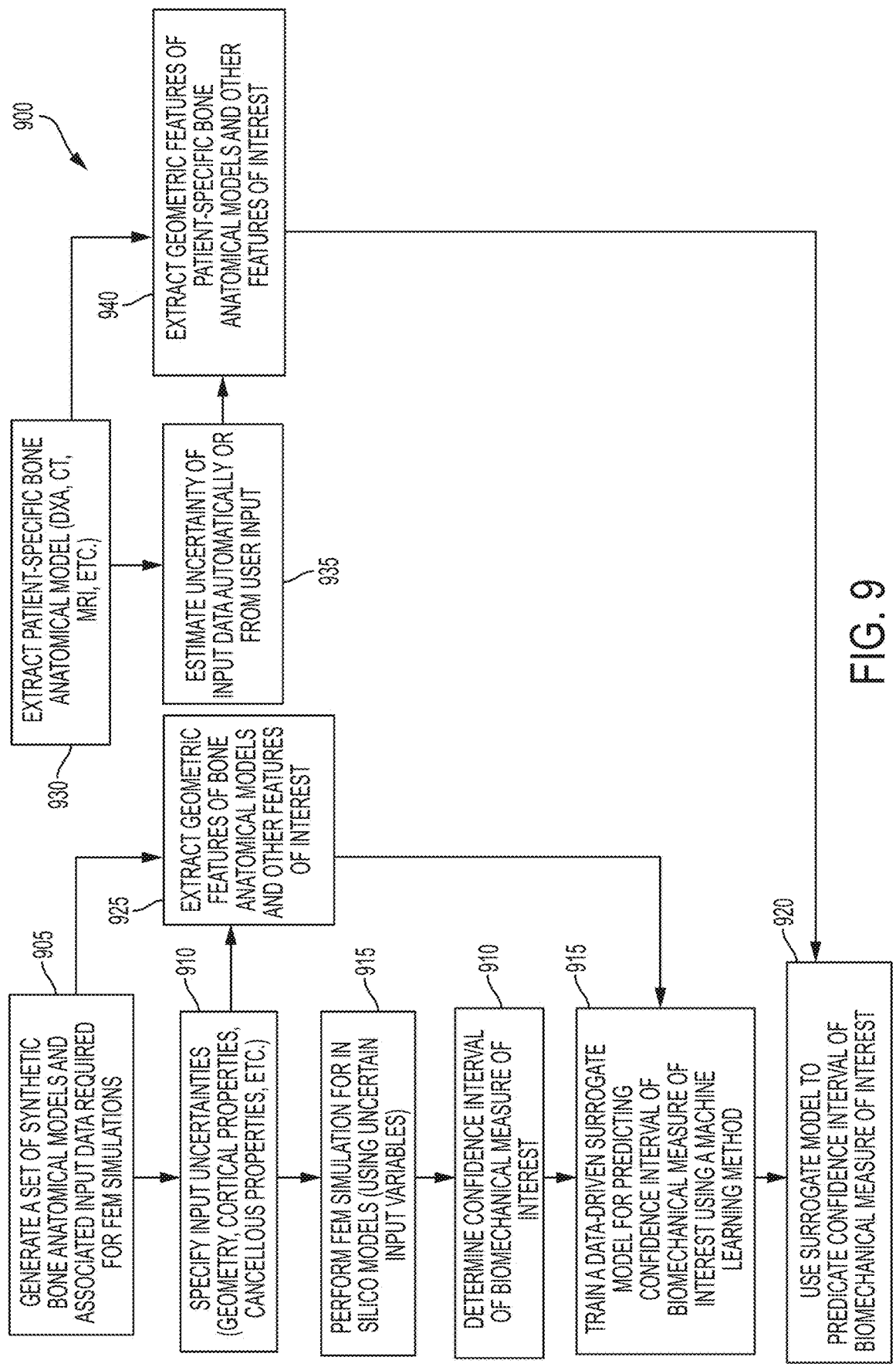
FIG. 9 shows a workflow used for estimating the uncertainty of the biomechanical measure of interest using a machine learning algorithm, according to some embodiments.

FIG. 9 illustrates a workflow that may be used for estimating the uncertainty of the biomechanical measure of interest metric using a machine learning algorithm, according to some embodiments. Separate machine learning algorithms may additionally be used to provide a confidence interval for the estimation of a biomechanical measure of interest related to osteoporosis. Since such an ML algorithm requires a large database, this example specifically refers to the use case where the database is composed of synthetic data, but a database containing synthetic and/or patient-specific data may be likewise used.

Starting at step 905, the synthetic bone anatomical models and associated input data required for FEM simulations is generated. At step 910, input uncertainties (geometry, cortical properties, cancellous properties, etc.) are specified. These input uncertainties are used at step 925 to extract geometric features of the bone anatomical models and other features of interest. Additionally, the input uncertainties are used at step 915 to perform FEM simulation for in-silico models (using uncertain input variables). After the FEM simulation, the confidence interval of biomechanical measure of interest is determined at step 916. Next, at step 918 a data-drive surrogate model is trained to predict the confidence interval of biomechanical measure of interest using an ML method. Thus, effectively, the uncertainty is learned through ML based on the extracted features.

Continuing with reference to FIG. 9, at step 930, patient-specific bone anatomical models are extracted (e.g., DXA, CT, MRI, etc.). This model is used to estimate the uncertainty of the input data at step 935, either automatically or from user input. At step 940, geometric features of the patient-specific bone anatomical models and other features of interest are extracted. Finally, at step 920, the surrogate model is used to predict a confidence interface of biomechanical measure of interest based on the data extracted at step 940.

Figure 10:
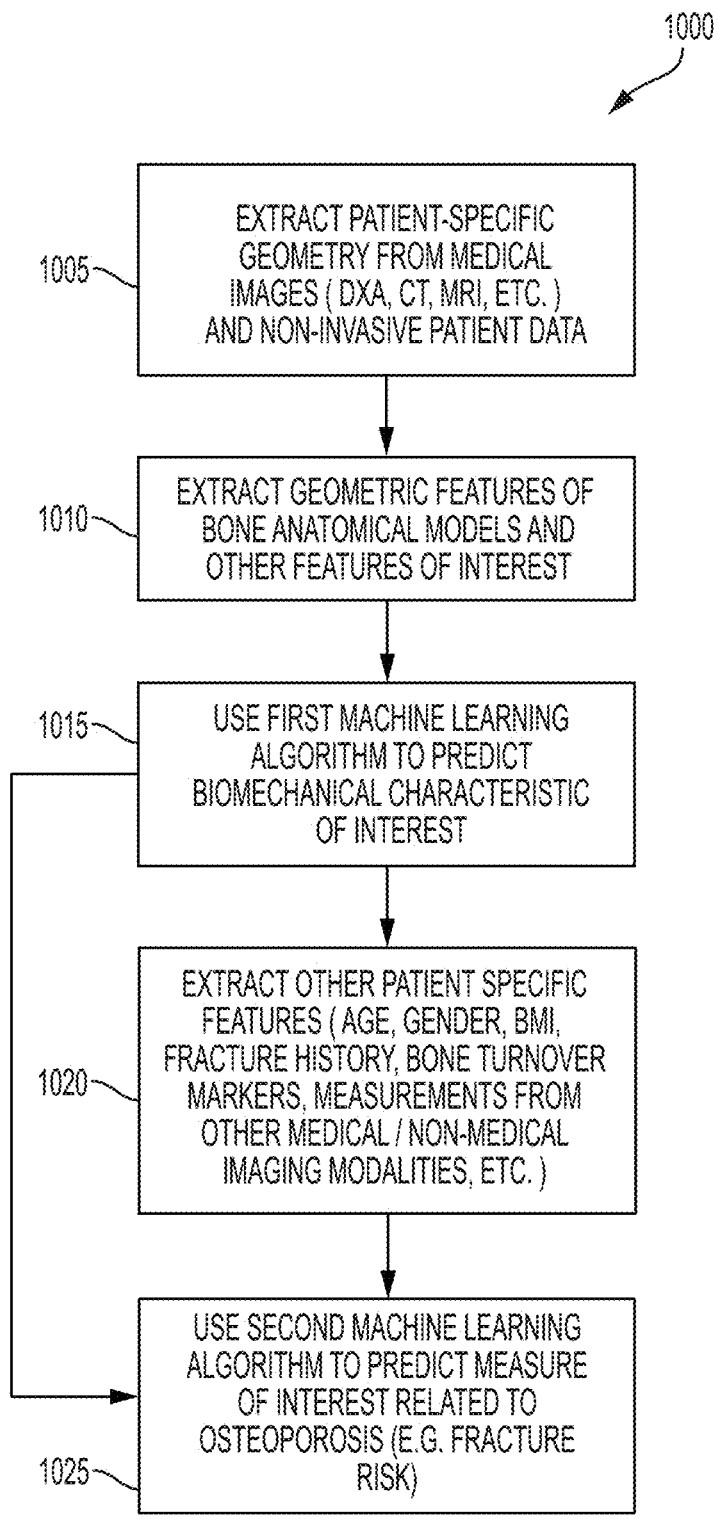
FIG. 10 illustrates a cascaded machine learning approach that may be used in some embodiments.

FIG. 10 displays an example of the workflow 1000 with a cascaded ML approach, according to some embodiments. Starting at step 1005, patient-specific geometry information is extracted from medical images and non-invasive patient data. Next, at step 1010, geometric features of the bone anatomical models and other features of interest are extracted. Then, at step 1015, a first machine learning algorithm trained purely on synthetic data is used to predict a biomechanical characteristic of interest.

Continuing with reference to FIG. 10, at step 1020, additional patient-specific features are extracted from biomechanical characteristics of interest. These additional features may include, for example, age, gender, BMI, fracture history, bone turnover markers, measurements from other medical/non-medical imaging modalities, etc. At step 1025 a second ML algorithm uses the result predicted by the first algorithm at step 1015 as feature, alongside the other patient-specific features extracted at step 1020, in order to obtain the final prediction of a measure of interest related to osteoporosis (e.g., fracture risk).

Figure 11:
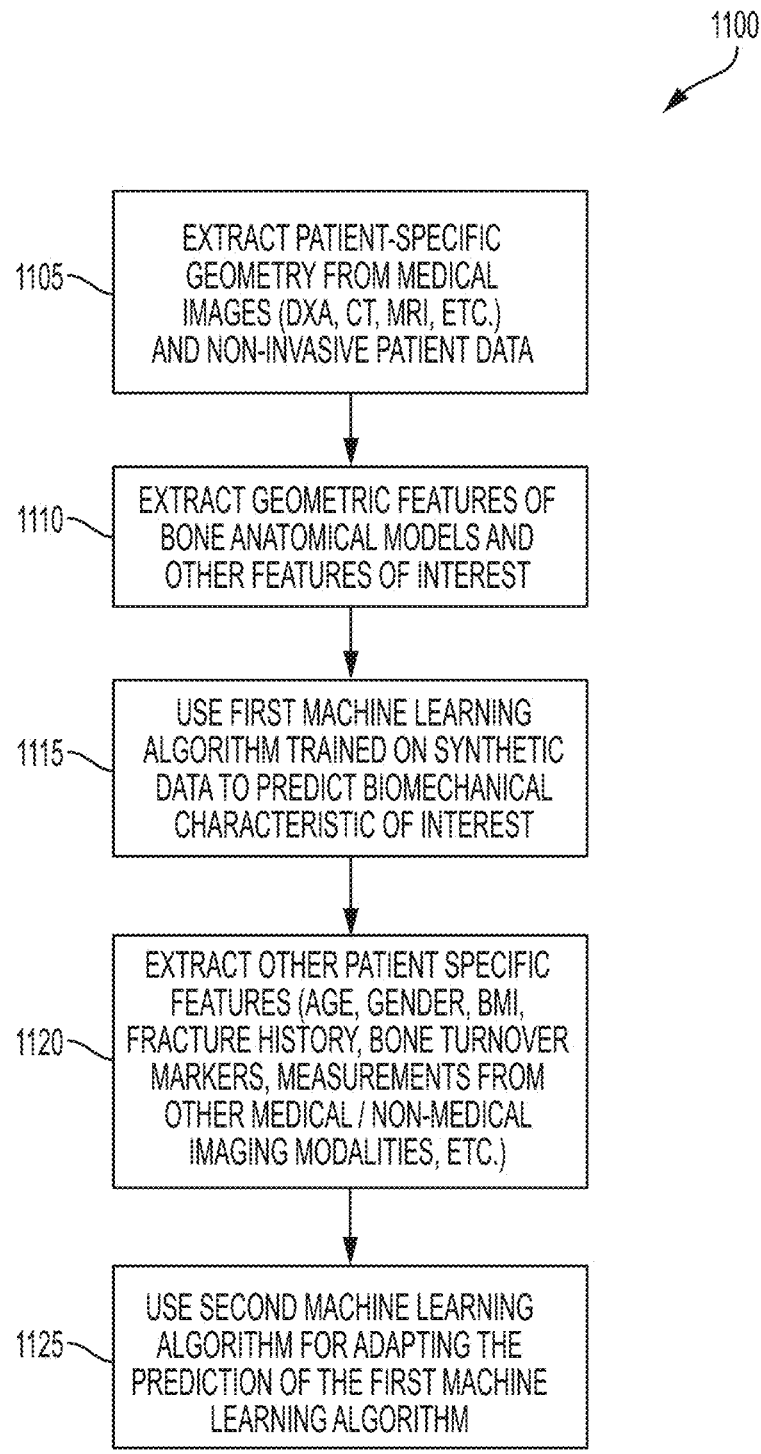
FIG. 11 depicts a cascaded machine learning approach for prediction correction that may be used in some embodiments.

In some embodiments, the second machine learning model may predict the same quantity as the first machine learning, but the first machine learning model may use only synthetic data, and the second machine learning model may additionally include patient-specific data, and, thus, act as a corrector of the prediction generated by the first ML model. FIG. 11 displays an example of such an approach, according to some embodiments. Steps 1105 and 1110 are substantially similar to steps 1005 and 1010 discussed above with reference to FIG. 11. At step 1115, a biomechanical characteristic of interest is predicted using a first machine learning algorithm which is trained on synthetic data. Step 1120 extracts patient-specific features based on the biomechanical characteristic of interest in a manner which is similar to step 1020 in FIG. 10. Finally, at step 1125, a second machine learning algorithm is used to adapt the prediction of the first ML algorithm.

Figure 12:
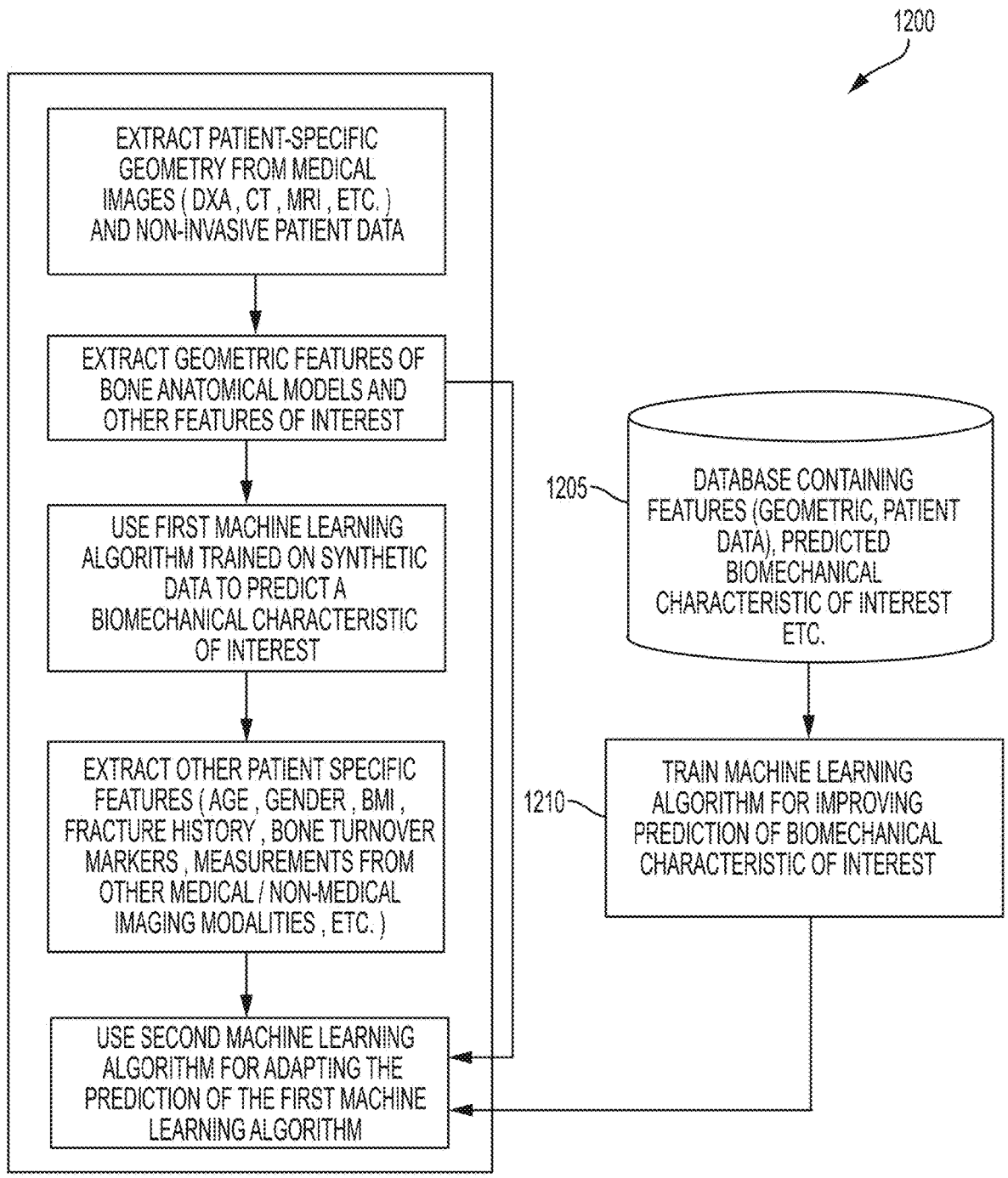
FIG. 12 shows a cascaded machine learning algorithm with database of patient-specific data, according to some embodiments.

Another possibility is to build a database with the patient-specific data of previous cases and to use this database during the sequential ML approach, as shown in FIG. 12. The shaded portion of FIG. 12 is substantially similar to the technique with respect to FIG. 11. As described before, during the first step, the ML algorithm learned on synthetic data is used to generate a first prediction of the measure of interest. During the second step, the features extracted for the patient specific data are used to find similar cases in the patient database and a second machine learning algorithm is applied for predicting the final value of the measure of interest. In this case, data is retrieved from a database 1205 and used at step 1210 to train the ML algorithm for improving prediction of the biomechanical characteristic of interest. The data retrieved from database 1205 may include, for example, features (geometric, patient data, etc.) and/or data regarding the predicted biomechanical characteristic of interest.

An important application in the context of clinical osteoporosis management is therapy planning. A ML-based workflow may be used to estimate the effect of different treatment plans and chose the best possible treatment plan for each patient, as illustrated in the example workflow shown in FIG. 13. Briefly, at step 1305 patient-specific geometry is extracted from medical/non-medical images, non-invasive patient data, and bone turnover markers. At step 1310, geometric features of bone anatomical models and other features of interest are extracted. Then, at step 1315, an ML model is used to predict the effect of a treatment plan.

Figure 13:
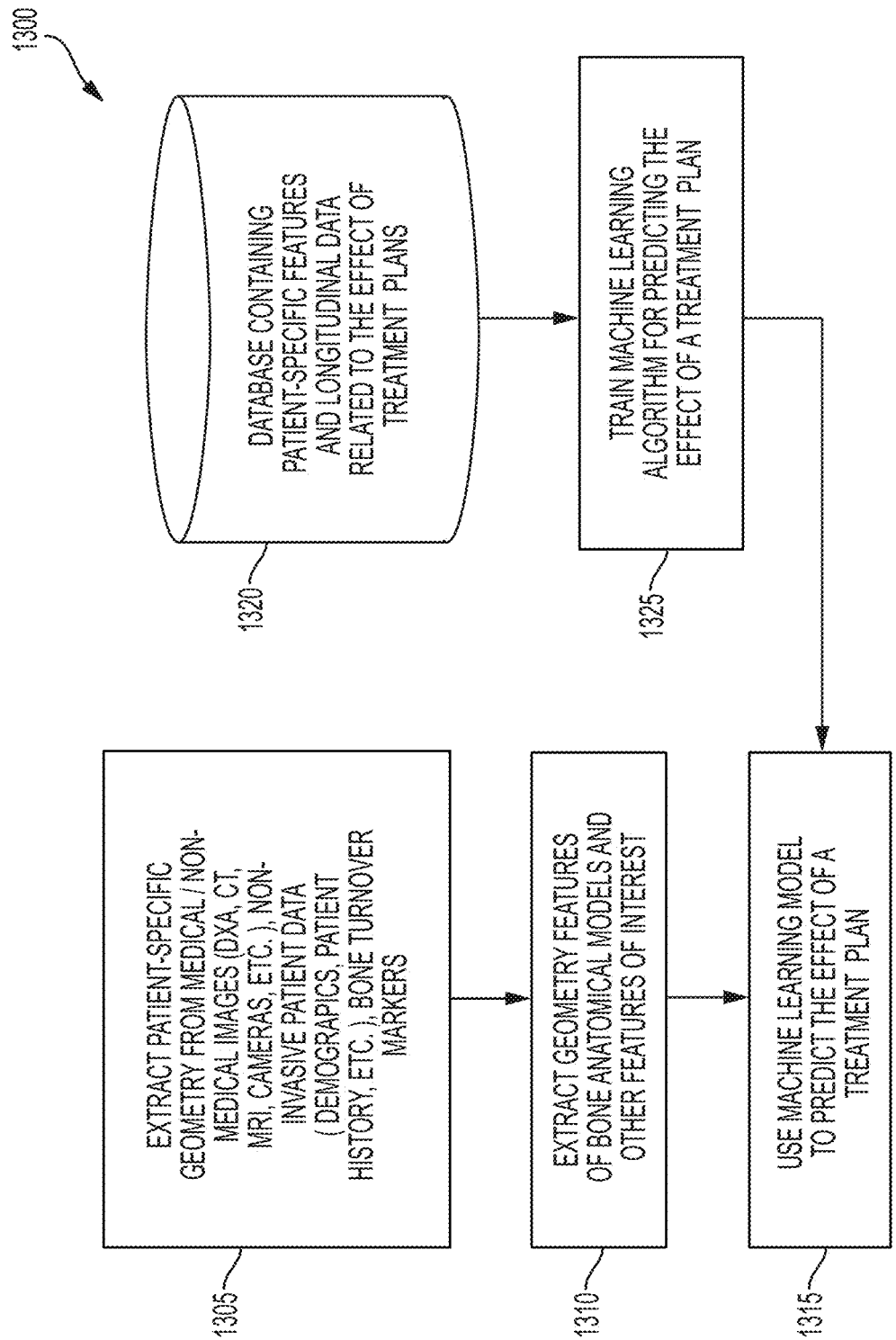
FIG. 13 illustrates a machine learning based workflow for predicting the effect of a treatment plan, according to some embodiments.

A crucial element for the workflow 1300 shown in FIG. 13 is the existence and use of a database 1320 comprising longitudinal data related to different treatment plans for various patients. Based on the data in this database 1320, ML models may be trained at step 1325 for different drugs (teriparatide, alendronate, denosumab, romosozumab, raloxifene), different combinations of drugs, assessing the effect of changes in treatment plans, and patients which have already suffered fractures, and patients without fractures.

Using the workflow 1300, the outcome measures of interest predicted by the ML model may be: optimal treatment plan (which drug, which quantity), improvement in bone strength after a certain period of time, decrease of fracture risk score, etc. Additionally, a cascaded ML approach may be used as described in the previous section: the first ML model focuses on the prediction of biomechanical characteristics of interest and the second ML model focuses on the prediction of the effect of the treatment plan.

Figure 14:
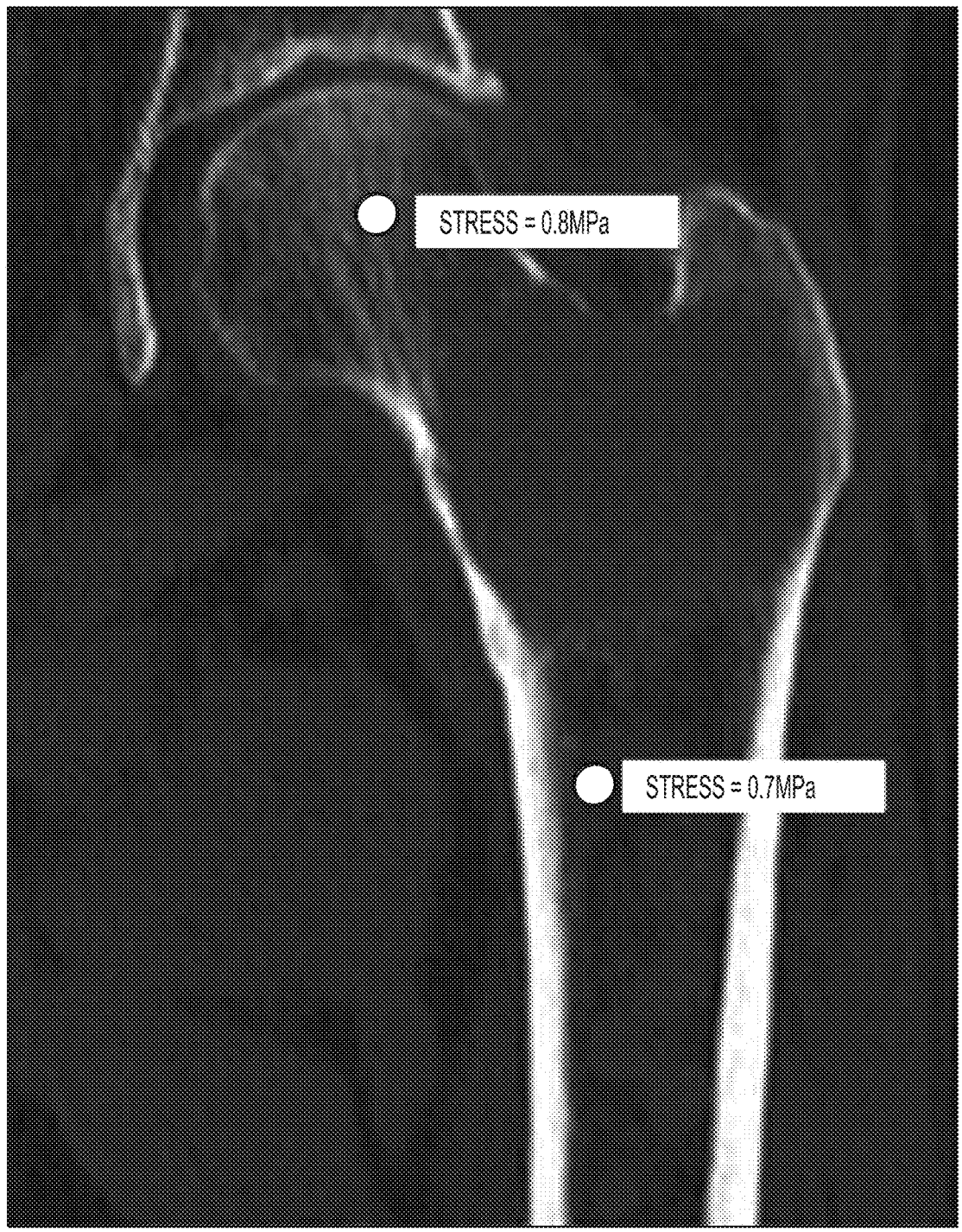
FIG. 14 depicts examples of a tool to point and click points on an image, where the system visualizes the point and the associated value of interest, according to some embodiments.

Computed results can be visualized on the scanner, or on another device, such as an imaging workstation. In case the measure of interest is a biomechanical characteristic any point on the image can be queried (point & click) for the associated value of the measure of interest, and the corresponding value is shown overlaid to the image. As an example, points of interest in the femur bone can be selected and the corresponding stress values shown in the image as demonstrated in FIG. 14. Alternatively, the user can activate a "no click" mode, in which case the value of interest is displayed in correspondence of the cursor by just positioning the cursor on the position of interest.

Alternatively (or additionally), a system may provide a touch screen enabling interactions with the anatomical object of interest (gestures to rotate, zoom, pan). Point & touch causes the system to display the value of interest at the point of touch. Furthermore, the anatomical model of the bone may be color coded based on the values of the measure of interest (a continuous or a discrete color map may be used for this purpose). The above mentioned approaches may be used for a 3D or 2D visualization, which may be based on projections of the results on a plane. In some embodiments, the measure of interest may also be visualized on the skeleton of the bone. Moreover, the measures of interest may be displayed interactively to changes in the feature set. If the user chooses to alter the value of any feature, it can instantly be reflected in the value of the computed measures.

In case of using different modalities or different acquisitions from the same modality (one for feature extraction, another one for visualization) registration of the images and features (spatial and temporal) is an important prerequisite. This can be done, for example, by specifying information of the image systems (in case they are registered), running algorithms on the images, or manually by the user by selecting land marks. In case of using the same scanner during examination and visualization, features can be table position, angulations, etc. If the measure of interest is a value representative for the entire anatomical model (e.g., whole bone strength), this value may be displayed on a screen together with associated ranges of normal, low risk and high risk values, color-coded or not.

The following presents results obtained for a sample implementation of a specific variant of the workflows described above. Synthetic cancellous geometries were created and meshed in order to conduct FEM simulations. Average strain was computed over all the finite elements. Features of the cancellous structures were extracted and used as features for the training of a neural network in order to predict the average strain. Average strain is an indication of the effect of a load for the structural deformation. If the average strain is close to the yield strain, plastic deformation will occur beyond that point. Accordingly, the yield strain can be computed based on the site of the analyzed bone structure (i.e. vertebra, femur) and apparent density, i.e., a typical cancellous compressive yield strain would be 0.84%.

The prediction accuracy was 91.9% for the cross-validation performed on synthetic geometries and 95% for patient-specific structures of cancellous tissue. The accuracy was computed as follows: for each strain prediction made by the neural network, the absolute relative error was determined. The average error (over all test entries) was subtracted from 1 and the final result multiplied by 100 gave the accuracy in percentage.

Figure 15:
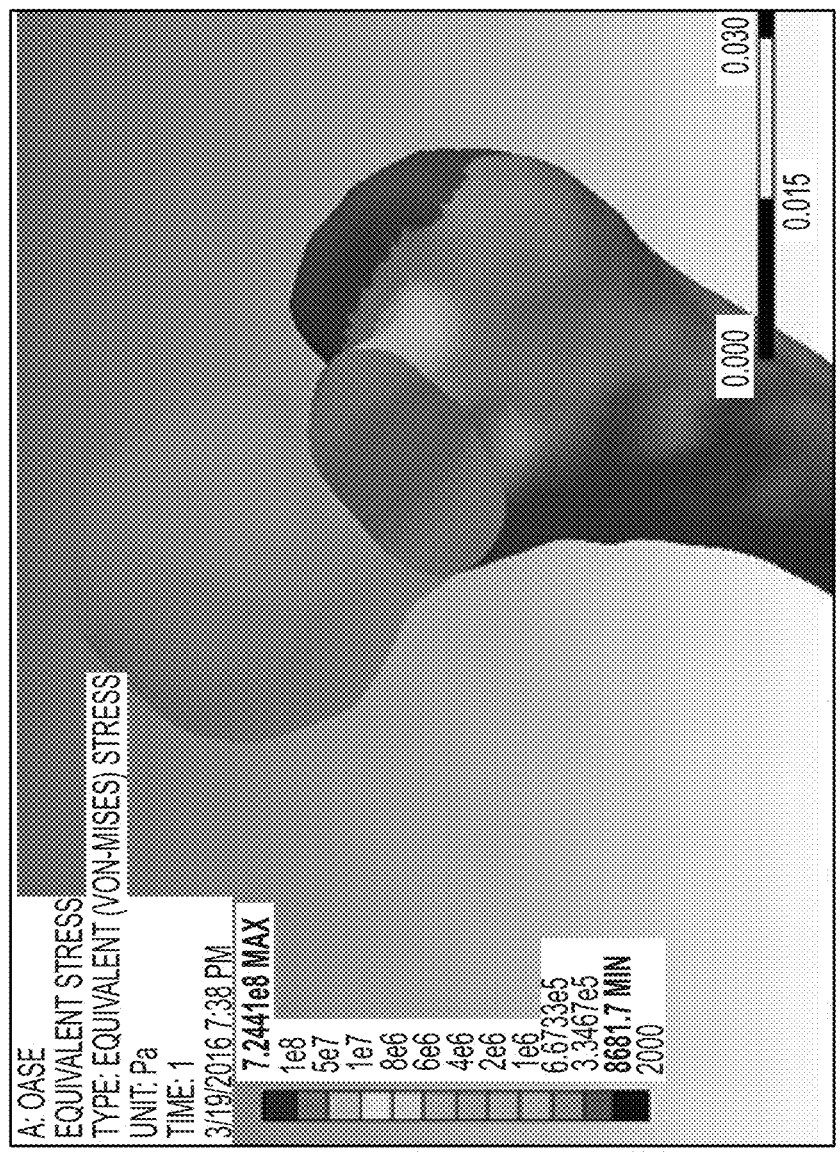
FIG. 15 shows stress results obtained after performing an organ level loading simulation for a human femur bone.

The synthetic data generation algorithm was described above. The resulting binary matrix was meshed and a finite element model was created. Each "1" in the binary matrix was meshed as a cube of side length equal to 0.15936 mm (Young modulus was assumed 17 GPa and Poisson's ratio 0.3). As a boundary condition, the bottom layer of nodes was fully constrained. The combined load on the Oz axis for the top layer nodes was computed so that the whole structure would support a prescribed weight. This weight was derived from an organ level simulation of a femur (see FIG. 15): a femur (modeled as an isotropic material) was loaded with 90 kg using boundary conditions described herein. A slice was selected as visualized in the figure below (in the femoral neck) and the corresponding stress 'S' was noted. The prescribed weight used for the cancellous FEM simulation was computed by multiplying 'S' with the area of a 32 by 32 slice of voxels.

A finite element analysis was carried out on the cancellous model and the average (normal) strain was computed over all the finite elements. The features used to train and test the machine learning predictor were (i) total number of bone voxels present in the binary matrix; (ii) total number of bone voxels which also have a bone voxel next to it along positive Oz direction; (iii) total number of bone voxels which also have a bone voxel next to it along positive Oy direction; (iv) total number of bone voxels which also have a bone voxel next to it along positive Ox direction; (v) total number of bone voxels which also have bone voxels next to it both for the Ox and Oy axis (along the positive and negative direction); (vi) total number of bone voxels which also have bone voxels next to it both for the Ox and Oz axis (along the positive and negative direction); and (vii) total number of bone voxels which also have bone voxels next to it both for the Oy and Oz axis (along the positive and negative direction).

A train dataset contacting 4000 geometries was created using the workflow described above and used to train a neural network. The patient-specific test dataset was obtained as follows: Two binary matrices (obtained from patient-data) were permuted (flipped, i.e. the orientation of the coordinate system was changed) in order to obtain six real-life geometries (three for each initial geometry). Also, a geometry rotated by 90 degrees around the Oz axis (which is the axis the weight was applied on) was created for each of the six resulting geometry. The rotation had the effect of swapping the values between some of the features, depending on the direction of rotation. This was used to test if the predicted strain was invariant to the Oz angular position of the structure in the base coordinate system (i.e. even if an object was rotated, it would behave the same because the load direction and the material structure itself were not changed). This yielded a total of 12 entries in the patient-specific test set.

The neural network predicted the strain (for the prescribed weight and for a Young's modulus equal to 17 GPa) using the seven features. Because the FEM simulation was linear, scaling the load by x % also scaled the strain by x %. Therefore, for a specific load, the final resulting strain could be computed by scaling the predicted value. Also, by scaling E (Young's Modulus) by ems, the resulting strain could be scaled by (1/ems). A linear simulation is valid for the majority of materials for small strains.

Figure 16A:
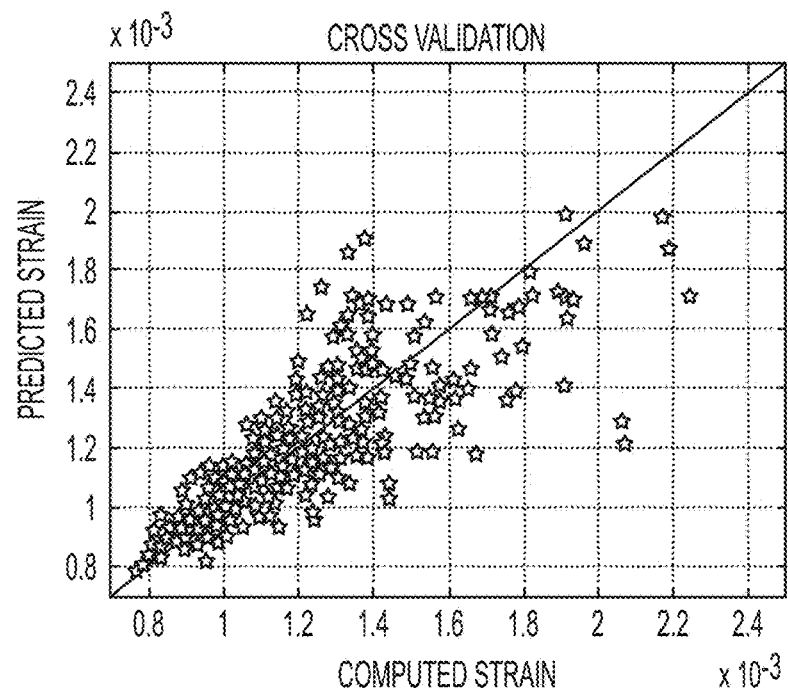
FIG. 16A illustrates a comparison of FEM-based computed strains and strains predicted by the ML algorithm for the cross-validation performed on the synthetic data and for the patient-specific data.
Figure 16B:
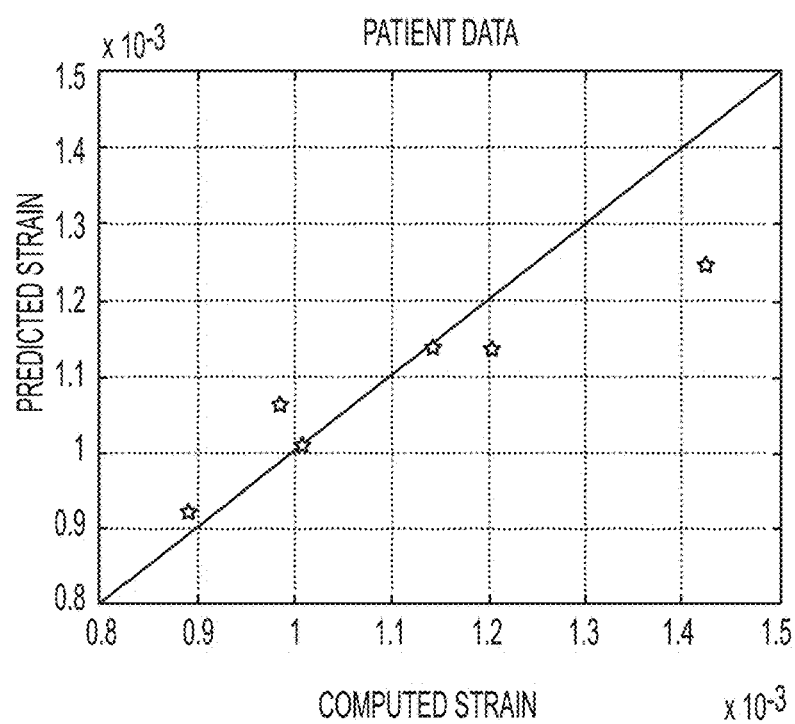
FIG. 16B illustrates a comparison of FEM-based computed strains and strains predicted by the ML algorithm for the cross-validation performed on patient-specific data

The neural network consisted of only one hidden layer with one neuron. This topology yielded good results and also avoided an overfitting of the training data. The accuracy was 91.9% for cross-validation (on the synthetic train dataset) and 95% for the patient-specific test data. Initial attempts only used the first four statistical properties as learning features and yielded only 90% accuracy for real data. FIGS. 16A and 16B provide a comparison of FEM-based computed strains and strains predicted by the ML algorithm for the cross-validation performed on the synthetic data (FIG. 16A) and for the patient-specific data (FIG. 16B). The correlation (Pearson's product-moment coefficient) between ground-truth and ML prediction was 0.845 for the cross-validation and 0.911 for the patient-specific data. The rotation of the geometry by 90 degrees around the Oz had no influence on the results, demonstrating that the ML prediction is robust with respect to this aspect.

To test the fracture/non-fracture classification capabilities of the ML predictor, the following synthetic setup was used: the synthetic dataset was split into two parts using random partitioning. The first part consisted of around 74% of all entries and represented the training set. The second part was used as the test set. A threshold strain value was chosen so that 70% of the entries in the synthetic dataset were below it and the rest of 30% above. This threshold strain value was considered to represent the cut-off value for the appearance of a fracture, i.e. the yield strain. The cut-off value was applied for the test set for both FEM and ML predicted strains. Classification capabilities (fracture/non-fracture) of the predictive model were determined. The confusion matrix and corresponding diagnostic statistics are displayed in FIG. 17.

In conclusion, the various workflows discussed herein may be employed to estimate patient-specific fracture risks: (i) acquire medical images of cancellous bone volume (e.g. using micro CT); (ii) create the corresponding binary matrix, based on the image dataset; (iii) extract the features from the binary matrix and estimate the apparent density; and (ii) feed the features to the trained neural network which, in turn, will predict the strain for the constantly prescribed force and for the implicit Young's modulus.

The workflows discussed herein may also be used to scale the predicted strain according to the patient weight and activity level. The predicted strain corresponds to a 90 kg load on the femur. For example, if the patient has a weight of 100 kg, the strain will be scaled by 100/90=1.11. Also, if the patient conducts activities which will peak the load up to, i.e., 150 kg, scale the strain by 150/90=1.66. Additionally, Young's modulus may be estimated from the apparent density. The strain that was computed during the previous step, scaled by E/estimated_E, where E=17 GPa is the implicit Young's modulus value used in the linear FEM simulation. For example, a power law relationship could be used to estimate Young's modulus as in: $E=a \times BMAD^b$, where a=16.1 GPa and b=1.37 for the inferior distal femur, BMAD is the bone mineral apparent density. Similar formulas, based on bone mineral density have been introduced in and for the vertebras and in for the femur bone. Additionally, the workflows may be used to compare the resulting strain to the site-specific yield strain (which is also a function of apparent density). The risk of fracture (in percentage) may be defined as resulting_strain/yield_strain*100.

Alternatively, if a non-linear FEM model is applied for generating the training data set, both the load and the Young's modulus can be used as features of the predictor and both properties may be varied across a large range of values when generating the training data set, so as to cover all possible values that may be encountered when applying the predictor for patient-specific data.

Various additional features, extensions, and variations may be added to the techniques and technology described herein. For example, in case only 2D images are available, 2D-3D matching algorithms may be employed to generate 3D anatomical models to be used in the biomechanical analysis and prediction. If the ML models are used to predict biomechanical characteristics of interest, separate ML models may be employed for separate parts of the bone: e.g. for the femur bone separate models may be used for the head and neck area and for the shaft, or for the cortical volume and the cancellous volume. In some embodiments, the features that are used by the ML models may be based on one bone, and the prediction may be performed for another bone: e.g. feature may be extracted for the femur bone and predictions may be performed for a vertebrae.

The approaches described above are based on steady-state FEA. Alternatively, transient FEA may be performed and other biomechanical characteristics of interest may be predicted by the ML model, which are related to the non-stationary behavior of the bone. For example, in case fall conditions are simulated, to predict the outcome it may be important to correctly take into account the slopes and duration of the specific load conditions.

In some embodiments, a wearable sensor system/mobile device may be used to measure different loading conditions for the patient during daily activities. These may be used for specifying different sets of boundary conditions for the FEM based computations and also as features for the prediction of various measures of interest.

The techniques discussed herein may also have additional clinical applications other than those discussed above. For example, approaches similar to the ones described herein may be used to determine optimal treatment plans for patients with bone fractures which may or may not be related to osteoporosis: e.g. use metallic plates, rods, gypsum, etc. Additionally (or alternatively), approaches similar to the ones described herein may be used to assess patients with one of the following bone disorders: avascular necrosis or osteonecrosis, bone spur (osteophytes), fibrodysplasia ossificans progressive, fibrous dysplasia, Fong Disease or Nail-patella syndrome, giant cell tumor of bone, greenstick fracture, hypophosphatasia, hereditary multiple exostoses, Klippel-Feil syndrome, metabolic bone disease, multiple myeloma, osteoarthritis, osteitis deformans (or Paget's disease of bone), osteitis fibrosa cystica (or osteitis fibrosa, or Von Recklinghausen's disease of bone), osteitis pubis, condensing osteitis (or osteitis condensas), osteochondritis dissecans, osteochondroma (bone tumor), osteogenesis imperfecta, osteomalacia, osteomyelitis, osteopetrosis, porotic hyperostosis, primary hyperparathyroidism, renal osteodystrophy, Salter-Harris fractures.

The advantage of ML algorithms is that the online prediction is extremely fast: it outputs results almost instantaneously (in a matter of seconds). Hence, they can be run directly on the workstation on-site. However, there may be situations in which a hybrid on-site-off-site processing workflow is required. For example, off-site processing can provide more detailed information or additional information that would not be available on-site, which is enabled by the less strict requirement on the processing time. Examples of such scenarios include employing a different computational model available off-site (e.g. FEM based) but not on-site, providing different analyses or options as compared to the on-site processing (e.g. therapy planning may only be available off-site); or running multiple computational models off-site, and reporting their results in a combined way; or accessing an updated version of the computational model or of the training database that is only available off-site.

On-site assessment may not be available at the time when the medical images are acquired. This may be due for instance to limitations of the imaging workstation (incompatible hardware or software configuration), or unavailability of the workstation providing the processing functionality. In this case, off-site processing can be offered as an alternative, to produce the same results as the on-site counterpart, or with the possibility of choosing different analyses or options.

The on-site assessment may be inconclusive or uncertain due to limitations of the predictor (e.g. the data set being processed has features outside the range considered in the training set). In this case, the off-site processing can include re-training the machine learning algorithm so that the feature values of the new case are within those of the training dataset. Alternatively, a different method can be used in the off-site processing step, such as computational modeling, that does not have the same limitation.

The on-site assessment can be inconclusive or uncertain due to intrinsic uncertainty of the quantity of interest (e.g. computed bone strength close to the cut-off value of a likely fracture). In this case, off-site processing can include consulting medical experts (human or databases) to find the best course of action for instance based on previous clinical cases with similar characteristics.

In another scenario, the on-site assessment provides a first approximation of the quantity of interest (for instance, not all image features can be extracted with confidence); in this case, off-site processing can include further image processing to extract more image features or with more confidence/less uncertainty. Off-site processing can also include evaluating a larger set of features (e.g. non-image features such as clinical history of the patient, risk factors for fractures, etc.) that can be incorporated in the predictor to improve the assessment.

If the same type of data is available at different time points (e.g. DXA): the data acquired at the current time point is analyzed on-site and then sent off-site for a comparative analysis with the previous acquisition. This may be used to determine the evolution of the pathology/patient so as to propose the optimal treatment strategy.

At the off-site processing site a parallel processing system can be used to minimize the overall processing of the algorithms. Of course, such a system may alternatively be applied on-site if it is available.

Figure 18:
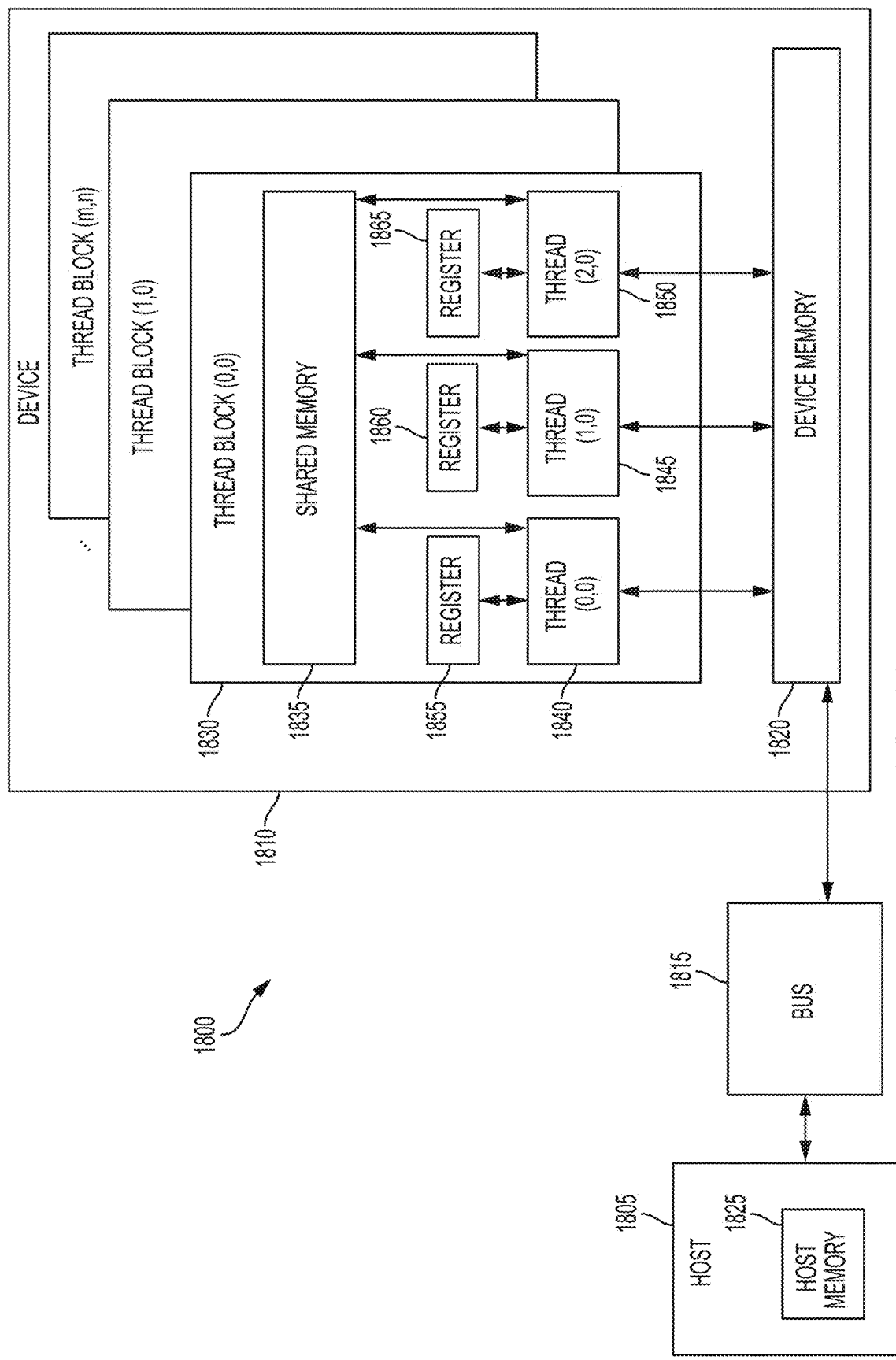
FIG. 18 provides an example of a parallel processing memory architecture that may be utilized to perform computations related to execution of the various workflows discussed herein, according to some embodiments of the present invention.

FIG. 18 provides an example of a parallel processing memory architecture 1800 that may be utilized to perform computations related to execution of the various workflows discussed herein, according to some embodiments of the present invention. This architecture 1800 may be used in embodiments of the present invention where NVIDIA™ CUDA (or a similar parallel computing platform) is used. The architecture includes a host computing unit ("host") 1805 and a graphics processing unit (GPU) device ("device") 1810 connected via a bus 1815 (e.g., a PCIe bus). The host 1805 includes the central processing unit, or "CPU"

(not shown in FIG. 18), and host memory 1825 accessible to the CPU. The device 1810 includes the graphics processing unit (GPU) and its associated memory 1820, referred to herein as device memory. The device memory 1820 may include various types of memory, each optimized for different memory usages. For example, in some embodiments, the device memory includes global memory, constant memory, and texture memory.

Parallel portions of a deep learning application may be executed on the architecture 1800 as "device kernels" or simply "kernels." A kernel comprises parameterized code configured to perform a particular function. The parallel computing platform is configured to execute these kernels in an optimal manner across the architecture 1800 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by grid of thread blocks (described in greater detail below). Using concurrent kernel execution, streams, and synchronization with lightweight events, the architecture 1800 of FIG. 18 (or similar architectures) may be used to parallelize training of a deep neural network. For example, in some embodiments, the operations of the simulation platform may be partitioned such that multiple kernels execute simulated different configurations simultaneously (e.g., different viewpoints, lighting, textures, materials, effects, etc.). In other embodiments, the deep learning network itself may be implemented so that various operations performed with the training and use of the network are done in parallel.

The device 1810 includes one or more thread blocks 1830 which represent the computation unit of the device 1810. The term thread block refers to a group of threads that can cooperate via shared memory and synchronize their execution to coordinate memory accesses. For example, in FIG. 18, threads 1840, 1845 and 1850 operate in thread block 1830 and access shared memory 1835. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 18, the thread blocks 1830 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints. To address this limitation, workflow operations may be configured in various manners to optimize use of the parallel computing platform. For example, in some embodiments, various stages of feature extraction may be performed in parallel. Additionally (or alternatively), the ML algorithm used during the various prediction phases described herein may be selected and adapted based on the ability of the algorithms to be parallelized. Thus, for example, certain neural network algorithms may be preferable where operations associated with predictions of measures of interest can be performed in parallel.

Continuing with reference to FIG. 18, registers 1855, 1860, and 1865 represent the fast memory available to thread block 1830. Each register is only accessible by a single thread. Thus, for example, register 1855 may only be accessed by thread 1840. Conversely, shared memory is allocated per thread block, so all threads in the block have access to the same shared memory. Thus, shared memory 1835 is designed to be accessed, in parallel, by each thread 1840, 1845, and 1850 in thread block 1830. Threads can access data in shared memory 1835 loaded from device memory 1820 by other threads within the same thread block (e.g., thread block 1830). The device memory 1820 is accessed by all blocks of the grid and may be implemented using, for example, Dynamic Random-Access Memory (DRAM).

Each thread can have one or more levels of memory access. For example, in the architecture 1800 of FIG. 18, each thread may have three levels of memory access. First, each thread 1840, 1845, 1850, can read and write to its corresponding registers 1855, 1860, and 1865. Registers provide the fastest memory access to threads because there are no synchronization issues and the register is generally located close to a multiprocessor executing the thread. Second, each thread 1840, 1845, 1850 in thread block 1830, may read and write data to the shared memory 1835 corresponding to that block 1830. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 1810 to read and/or write to the device memory. Device memory requires the longest time to access because access must be synchronized across the thread blocks operating on the device. Thus, in some embodiments, the processing of each seed point is coded such that it primarily utilizes registers and shared memory and only utilizes device memory as necessary to move data in and out of a thread block.

The embodiments of the present disclosure may be implemented with any combination of hardware and software. For example, aside from parallel processing architecture presented in FIG. 18, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A computer-implemented method for personalized assessment of a subject's bone health, the method comprising:
   extracting a plurality of features of interest from non-invasive subject data, medical images of the subject, and subject-specific bone turnover marker values;
   using a surrogate model and the plurality of features of interest to predict one or more subject-specific measures of interest related to bone health; and
   generating a visualization of the one or more subject-specific measures of interest related to bone health;
   wherein the surrogate model is trained by a process comprising:
      retrieving training data comprising one or more of (i) a plurality of bone anatomical models and (ii) a plurality of in-vitro models from a database;
      performing FEM-based computations using the plurality of bone anatomical models or stress-experiments using the plurality of in-vitro models to yield FEM results;
      extracting one or more measures of interest from the FEM results;
      extracting a plurality of geometric features from the plurality of bone anatomical models; and
      training the surrogate model to predict the one or more measures of interest based on the plurality of geometric features using a machine learning algorithm.

2. The method of claim 1, wherein the measures of interest comprise one or more of stress and stress strain.

3. The method of claim 1, wherein at least a portion of the training data comprises synthetic data.

4. The method of claim 3, wherein the synthetic data is generated by:
   generating one or more baseline models;
   randomly or systematically perturbing the baseline models to obtain a plurality of synthetic models comprising one or more of (i) synthetic bone anatomical models and (ii) synthetic in-vitro models.

5. The method of claim 4, wherein the baseline models are subject-specific anatomical models.

6. The method of claim 3, wherein the synthetic data comprises one or more of (i) synthetic bone anatomical models and (ii) synthetic in-vitro models generated according to a set of rules using one or more randomly or systematically perturbed parameter values.

7. The method of claim 1, further comprising:
   associating each of the one or more subject-specific measures of interest with a point on a subject image; and
   displaying the subject image; and
   in response to receive a user selection of a selected point on the subject image, displaying a particular subject-specific measures of interest corresponding to the selected point.

8. The method of claim 1, further comprising:
   associating each of the one or more subject-specific measures of interest with a point on a subject image; and
   displaying the subject image color coded based on values of the subject-specific measures of interest.

9. A parallel processing computing system comprising:
   a host computer configured to extract a plurality of features of interest from non-invasive subject data, medical images of a subject, and subject-specific bone turnover marker values; and
   a device computer configured to use a surrogate model and the plurality of features of interest to predict one or more subject-specific measures of interest related to bone health,
   wherein the surrogate model is trained by a process comprising:
      retrieving training data comprising one or more of (i) a plurality of bone anatomical models and (ii) a plurality of in-vitro models from a database;
      performing FEM-based computations using the plurality of bone anatomical models or stress-experiments using the plurality of in-vitro models to yield FEM results;
      extracting one or more measures of interest from the FEM results;
      extracting a plurality of geometric features from the plurality of bone anatomical models; and
      training the surrogate model to predict the one or more measures of interest based on the plurality of geometric features using a machine learning algorithm.

* * * * *